(12) United States Patent
Gray

(10) Patent No.: US 7,671,594 B2
(45) Date of Patent: Mar. 2, 2010

(54) MAGNETIC RESONANCE IMAGING INTERFERENCE IMMUNE DEVICE

(75) Inventor: Robert W. Gray, Rochester, NY (US)

(73) Assignee: Medtronic, Inc., Minneapolis, MN (US)

( * ) Notice: Subject to any disclaimer, the term of this patent is extended or adjusted under 35 U.S.C. 154(b) by 139 days.

(21) Appl. No.: 11/697,254

(22) Filed: Apr. 5, 2007

(65) Prior Publication Data

US 2008/0079429 A1    Apr. 3, 2008

Related U.S. Application Data

(63) Continuation-in-part of application No. 10/887,533, filed on Jul. 8, 2004, which is a continuation-in-part of application No. 10/780,261, filed on Feb. 17, 2004, now Pat. No. 6,949,929.

(60) Provisional application No. 60/744,456, filed on Apr. 7, 2006, provisional application No. 60/744,457, filed on Apr. 7, 2006, provisional application No. 60/482,177, filed on Jun. 24, 2003.

(51) Int. Cl.
*G01V 3/001* (2006.01)

(52) U.S. Cl. ........................ 324/318; 324/322
(58) Field of Classification Search ......... 324/300–322; 600/407–445; 607/9
See application file for complete search history.

(56) References Cited

U.S. PATENT DOCUMENTS

| 5,217,010 | A | * | 6/1993 | Tsitlik et al. | 607/9 |
| 6,101,417 | A | * | 8/2000 | Vogel et al. | 607/30 |
| 6,198,972 | B1 | * | 3/2001 | Hartlaub et al. | 607/63 |
| 6,711,440 | B2 | * | 3/2004 | Deal et al. | 607/9 |
| 6,725,092 | B2 | * | 4/2004 | MacDonald et al. | 607/2 |
| 6,971,391 | B1 | * | 12/2005 | Wang et al. | 128/846 |

* cited by examiner

*Primary Examiner*—Brij B Shrivastav
(74) *Attorney, Agent, or Firm*—Michael J. Ostrom; Stephen W. Bauer

(57) ABSTRACT

A medical apparatus includes a medical assist device to process signals to relating biological functions. A first lead is operatively connected to the medical assist device, the first lead having a distal end and a proximal end. A second lead is operatively connected to the medical assist device, the second lead having a distal end and a proximal end. The first electrode is operatively connected to the distal end of the first lead, and a second electrode is operatively connected to the distal end of the second lead. A filter circuit is operatively connected near the distal end of the first lead and the distal end of the second lead. A compensation circuit, operatively connected to the first lead, provides a compensation voltage to enable the filter to effectively block changing magnetic fields induced current in the second lead from passing through the second electrode of the distal end of the second lead.

20 Claims, 18 Drawing Sheets

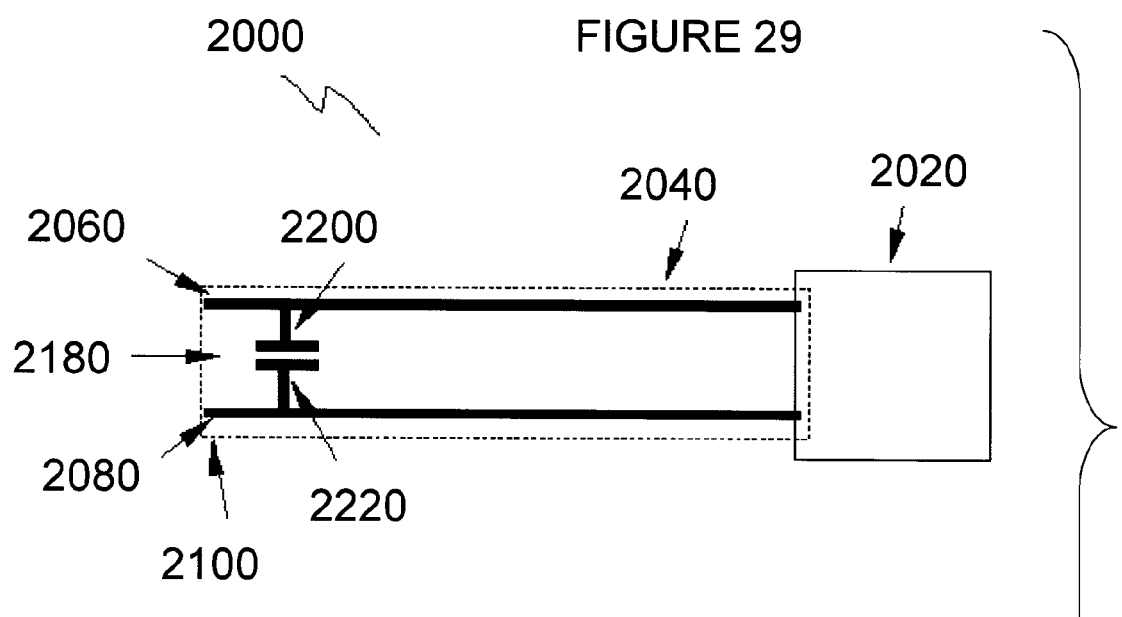
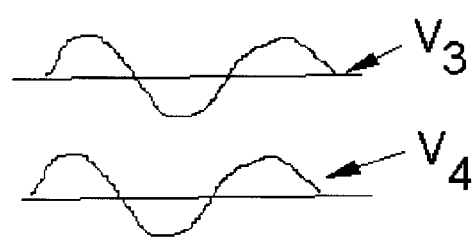
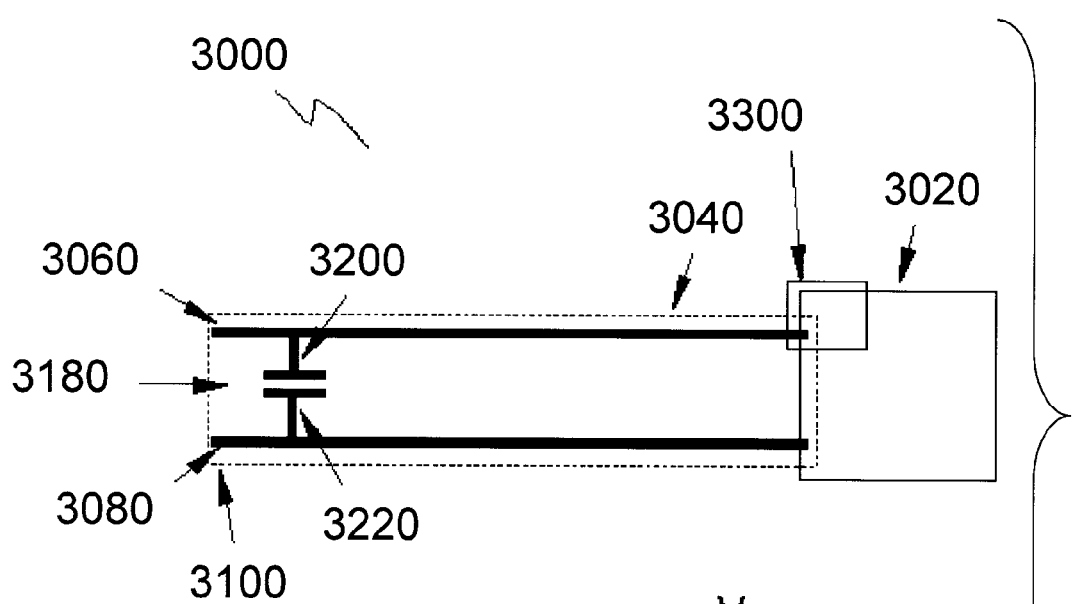
FIGURE 30
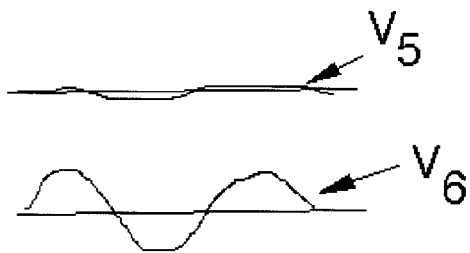

MAGNETIC RESONANCE IMAGING INTERFERENCE IMMUNE DEVICE

PRIORITY INFORMATION

The present application is a continuation-in-part of co-pending U.S. patent application Ser. No. 10/887,533, filed on Jul. 8, 2004, said co-pending U.S. patent application Ser. No. 10/887,743, filed on Jul. 8, 2004 is a continuation-in-part of U.S. patent application Ser. No. 10/780,261, filed on Feb. 17, 2004 (now U.S. Pat. No. 6,949,929). The entire contents of co-pending U.S. patent application Ser. No. 10/887,533, filed on Jul. 8, 2004, and U.S. Pat. No. 6,949,929 are hereby incorporated by reference. The entire content of U.S. patent application Ser. No. 11/248,862, filed on Oct. 12, 2005 is also hereby incorporated by reference.

The present application claims priority, under 35 U.S.C. §119(e), from U.S. Provisional Patent Application Ser. No. 60/744,456, filed on Apr. 7, 2006. The present application also claims priority, under 35 U.S.C. §119(e), from U.S. Provisional Patent Application Ser. No. 60/744,457, filed on Apr. 7, 2006. The entire contents of U.S. Provisional Patent Application Ser. No. 60/744,456, filed on Apr. 7, 2006, and U.S. Provisional Patent Application Ser. No. 60/744,457, filed on Apr. 7, 2006, are hereby incorporated by reference.

The present application claims priority, under 35 U.S.C. §120, from co-pending U.S. patent application Ser. No. 10/887,533, filed on Jul. 8, 2004 and from U.S. patent application Ser. No. 10/780,261, filed on Feb. 17, 2004. Said U.S. patent application Ser. No. 10/780,261, filed on Feb. 17, 2004 claimed priority, under 35 U.S.C. §119(e), from U.S. Provisional Patent Application Ser. No. 60/482,177, filed on Jun. 24, 2003. The present application claims priority, under 35 U.S.C. §119(e), from U.S. Provisional Patent Application Ser. No. 60/482,177, filed on Jun. 24, 2003. The entire content of U.S. Provisional Patent Application Ser. No. 60/482,177, filed on Jun. 24, 2003, is hereby incorporated by reference.

FIELD OF THE PRESENT INVENTION

The present invention is directed to a device for protecting a patient, physician, and/or electronic components in an electrical device implanted or partially implanted within the patient. More particularly, the present invention is directed to a device for reducing or substantially eliminating current and/or voltage surges induced by magnetic resonance imaging systems' oscillating magnetic fields.

BACKGROUND OF THE PRESENT INVENTION

Magnetic resonance imaging has been developed as an imaging technique adapted to obtain both images of anatomical features of human patients as well as some aspects of the functional activities and characteristics of biological tissue. These images have medical diagnostic value in determining the state of the health of the tissue examined. Unlike the situation with fluoroscopic imaging, a patient undergoing magnetic resonance imaging procedure may remain in the active imaging system for a significant amount of time, e.g. a half-hour or more, without suffering any adverse effects.

In a magnetic resonance imaging process, a patient is typically aligned to place the portion of the patient's anatomy to be examined in the imaging volume of the magnetic resonance imaging apparatus. Such an magnetic resonance imaging apparatus typically comprises a primary electromagnet for supplying a constant magnetic field ($B_0$) which, by convention, is along the z-axis and is substantially homogeneous over the imaging volume and secondary electromagnets that can provide linear magnetic field gradients along each of three principal Cartesian axes in space (generally x, y, and z, or $x_1$, $x_2$ and $x_3$, respectively). The magnetic resonance imaging apparatus also comprises one or more radio frequency coils that provide excitation and detection of the magnetic resonance imaging induced signals in the patient's body.

The gradient fields are switched ON and OFF at different rates depending on the magnetic resonance imaging scan sequence used. In some cases, this may result in a changing magnetic field on the order of dB/dt=50 T/s. The frequency that a gradient field may be turned ON can be between 200 Hz to about 300 kHz.

For a single loop with a fixed area, Lenz's law can be stated as:

$$EMF = -A \bullet dB/dt$$

where A is the area vector, B is the magnetic field vector, and "●" is the vector scalar product. This equation indicates that an electro-motive-force (EMF) is developed in any loop that encircles a changing magnetic field.

In a magnetic resonance imaging system, there is applied to the biological sample (patient) a switched gradient field in all 3 coordinate directions (x-, y-, z-directions). If the patient has an implanted heart pacemaker (or other implanted devices having conductive components) the switched gradient magnetic fields (an alternating magnetic field) may cause erroneous signals to be induced/generated in a sensing lead or device or circuit; damage to electronics; and/or harmful stimulation of tissue, e.g. heart muscle, nerves, etc.

As noted above, the use of the magnetic resonance imaging process with patients who have implanted medical assist devices; such as cardiac assist devices or implanted insulin pumps; often presents problems. As is known to those skilled in the art, implantable devices (such as implantable pulse generators (IPGs) and cardioverter/defibrillator/pacemakers (CDPs)) are sensitive to a variety of forms of electromagnetic interference (EMI) because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures.

To more appreciate the problem, the use of implantable cardiac assist devices during a magnetic resonance imaging process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Moreover, problems are realized when the placement of the implant is next to particular organs. For example, when a pacemaker is placed in the upper chest and the lead tip is placed into the heart, a loop (an electrical loop) is created. A changing magnetic field (the switched gradient field) over the area of the loop (through the area of the loop) will cause an induced voltage (and current) across the heart. This induced voltage (current) can stimulate the heart inappropriately and can cause heart damage or death.

Therefore, it is desirable to provide a medical device or system that reduces or eliminates the undesirable effects of changing magnetic fields from a magnetic resonance imaging system on the medical devices and/or patients undergoing medical procedures or that have temporary or permanent implanted materials and/or devices with conducting components.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein:

FIG. 29 illustrates a pacing system with a lead including two conductors with a low pass filter being implemented by the insertion of a capacitor between the two conductors according to the concepts of the present invention;

FIG. 30 illustrates a pacing system comprising a lead, a pulse generator, and a voltage compensation component according to the concepts of the present invention;

DETAILED DESCRIPTION OF THE PRESENT INVENTION

Figure 1:
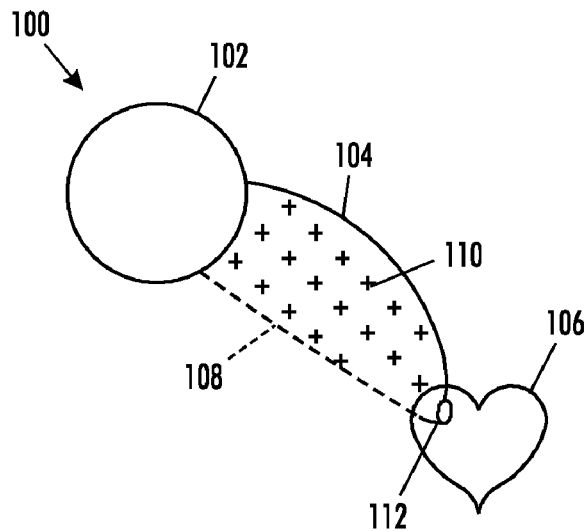
FIG. 1 is a schematic of an implanted pacemaker arrangement in a body.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention as defined by the appended claims.

For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

FIG. 1 is a schematic showing a typical pacemaker arrangement 100. The pacemaker comprises a pulse generator canister 102 housing a power supply (not shown) and electronic components (not shown) for sensing and producing electrical pacing pulses. The pulse generator canister 102 has connected to it insulated conductive leads 104 that pass through the body (not shown) and into the heart 106. Conventional bipolar pacemaker leads have two conductive strands, one for pacing and sensing, and the other for ground. The path of the leads 104 is generally not straight. The leads 104 have one or more electrodes 112 in contact with the heart 106. The path 108 from the heart 106, where the electrodes 112 are placed, to the generator canister 102 represents a conductive path comprising body tissue (not shown) and fluids (not shown). The completed loop from the pacemaker canister 102, through the leads 104, and back to the pacemaker canister 102 along the path 108 is subject to Lenz's law. That is, a changing magnetic field 110 through the area enclosed by the completed loop (from the pacemaker canister 102, through the leads 104, and back to the pacemaker canister 102 along the path 108) can induce unwanted voltages in the leads 104 and across the heart 106.

In one embodiment of the present invention, and referring to FIG. 1, the pacemaker canister 102 is made out of a non-conductive material. In another embodiment, the canister 102 is coated or covered with various non-conductive insulating materials. This increases the overall resistance of the conductive path loop and thus reduces the voltage across the tissue between electrodes 112 and the canister 102.

Using a three-strand lead design allows for the separation of the pacing signals from the sensing signals and allows for different filtering techniques to be utilized on each separate conductive strand: one strand for the pacing signal for stimulating the heart, one conductive strand for the sensing of the heart's electrical state, pre-pulse, ecg, etc., and one strand for the ground path. Current bi-polar designs use only two conductive strands. This means that the pacing and the sensing signals are carried on the same strand.

For example, in conventional bipolar pacemaker leads, the pacing signal goes "down" (from generator canister to heart) the pacing lead (conductive strand) while the sensing signal travels "up" (from heart to generator canister) the pacing lead. This is the "standard" bipolar pacing setup. If a filter is added to the pacing/sensing strand to block the switch gradient induced signal caused by a magnetic resonance imaging system, the pacing pulse/signal must travel through the filter, thereby distorting the pacing pulse.

According to the concepts of the present invention, by adding a third conductive strand, a diode, for example, can be put on the pacing strand and one or more filters can be put on the sensing strand. The filters on the sensing lead may be at the distal end of the pacemaker lead or in the generator canister. Thus, by using separate strands, the present invention is able to utilize different kinds of filters (radio-frequency filters, high/low pass filters, notch filters, etc.) or other electronics in conjunction with each strand depending on the different signal characteristics and/or signal direction along the conductive strand.

Figure 2:
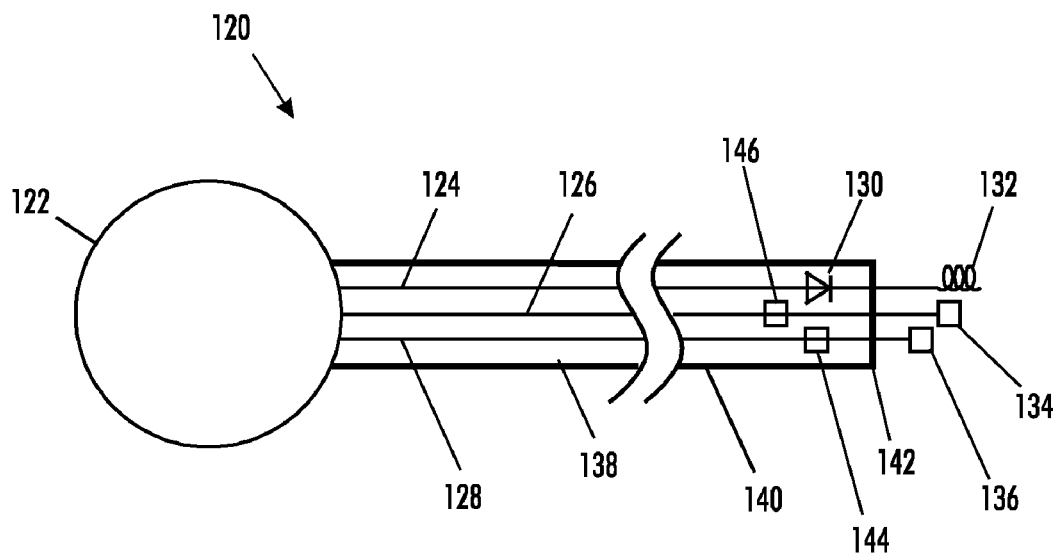
FIG. 2 is a schematic of a pacemaker lead comprising three conductive strands.

FIG. 2 shows a schematic of a pacemaker arrangement 120 including a generator canister 122 containing a pacing pulse generator (not shown), sensing electronics (not shown) and other electronic components (not shown). Attached to the generator canister 122 is a lead assembly 140 having three conductive strands 124, 126, and 128 through lumen 138. Each of the conductive strands 124, 126, and 128 pass through the distal tip 142 of the lead assembly 140 to exposed electrodes 132, 134, and 136, respectively. The exposed electrodes 132, 134, and 136 are placed in contact with or next to the heart.

Conductive strand 124 and electrode 132 are used to deliver pulses to the heart from a pacing generator within the canister 122. Conductive strand 126 and electrode 134 are used as a ground. Conductive strand 128 and electrode 136 are utilized for sensing the electrical signals generated by the heart. In this way, the sensing functionality of pacemakers can be separated from the delivery of pacing pulses.

To block any induced voltage signals from the magnetic resonance imaging system's changing magnetic fields (the radio-frequency or the gradient fields) from propagating along the conductive pulse delivery strand 124, a diode 130 is inserted into the conductive strand 124 near the distal tip of the lead assembly 142. In another embodiment (not shown), the diode 130 is placed in the generating canister 122.

With respect to FIG. 2, other electronic components (i.e. radio-frequency chocks, notch filters, etc.) may be placed into the other conductive strands 126 and 128 shown as by components 146 and 144, respectively. In another embodiment (not shown), these optional electronic components 146 and 144 can be placed in the generator canister 122.

Optional electronic components 146 and 144 are used to block or significantly reduce any unwanted induced signals caused by the magnetic resonance imaging system from passing along conductive strands 126 and 128 respectively while allowing the desired sensing signals from the heart to pass along conductive strand 126 to electronics in the generator canister 122.

Figure 3:
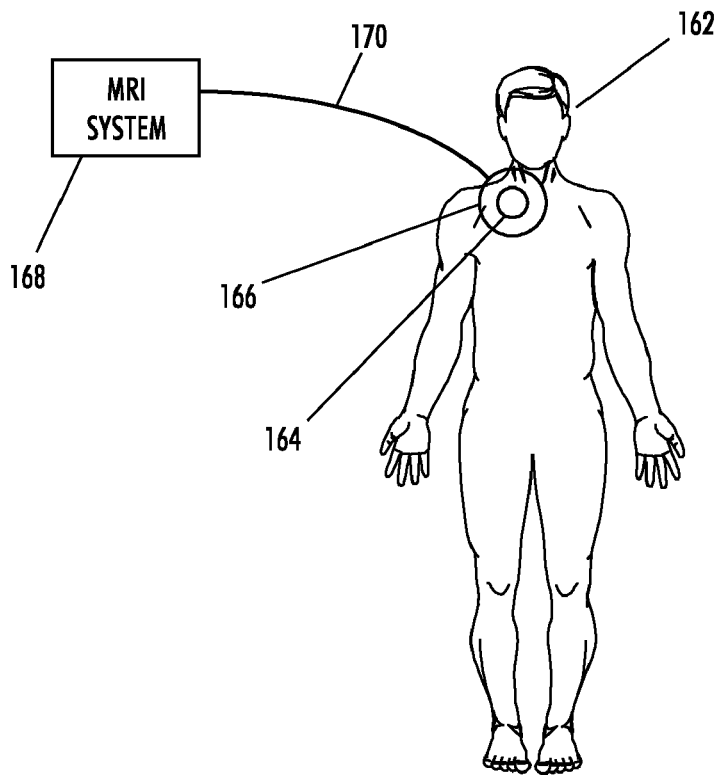
FIG. 3 is a schematic of a sensing system used with a pacemaker.

FIG. 3 is a schematic of an embodiment of the present invention. As illustrated in FIG. 3, a patient 162 is located within a magnetic resonance imaging system 168, wherein the patient 162 has an implanted heart pacemaker pulse generator canister 164. A surface sensor/transceiver 166 is placed on the exterior of the patient's body 162 over or near the location of the implanted pacemaker generator 164. The sensor/transceiver 166 is in communication with the magnetic resonance imaging system 168 via communication line 170, which may be a magnetic resonance imaging safe cable such as a fiber optical cable. Additionally, the sensor/transceiver 166 is in communication with the implanted pacemaker pulse generator canister 164. The means of communication between the sensor/transceiver 166 and the implanted pacemaker generator 164 may be acoustic, optical, or other means that do not interfere with the imaging capabilities or image quality of the magnetic resonance imaging system. The signals may be digital or analog.

Moreover, with respect to this embodiment of the present invention, a transmitter/receiver is placed in the pacemaker canister 164 so that the magnetic resonance imaging system 168 can be in operative communication with the pacemaker system and vice versa. Thus, the pacing system can transmit signals to the magnetic resonance imaging system 168 indicating when the pacemaker is about to deliver a pacing pulse to the heart. The transmitted signals may be digital or analog. In response to this transmitted signal, the magnetic resonance imaging system 168 stops or pauses the magnetic resonance imaging switched gradient field (imaging scanning sequence) to allow the pacing pulse to occur. After the pacing pulse has been delivered to the heart, the magnetic resonance imaging system 168 resumes or begins a new imaging scanning sequence.

In another mode of operation, the magnetic resonance imaging system 168 sends signals to the implanted heart pacemaker pulse generator canister 164 through the sensor/transceiver 166 indicating the application of switched gradient fields. The pacemaker may use this information to switch filters or other electronics in and out of the circuit to reduce or eliminate voltages induced in the pacemaker leads by the gradient fields. For example, the pacemaker may switch in additional resistance or inductance or impedance into the pacing/sensing and/or ground strands based on the signal from the magnetic resonance imaging system 168 signifying the application of the gradient fields.

In another configuration, there is no surface sensor/transceiver or communication line to the magnetic resonance imaging system 168. Instead, there is a special sensor in the implanted heart pacemaker pulse generator canister 164 that can sense the application of the gradient fields. In response thereof, the pacemaker switches into the electrical circuit of the pacing/sense and/or ground leads a charging source which is used to charge the implanted heart pacemaker pulse generator canister 164, leads, and/or electrodes to an electrical potential opposite to that which would be induced by the gradient fields. In this way, the induced voltages caused by the gradient fields are cancelled out or reduced to a safe level, by the application of this voltage source.

In a preferred embodiment of the present invention, the charging/voltage source receives its power from inductively coupling to the magnetic resonance imaging system's radio-frequency field. The oscillating radio-frequency field supplies power to charge special capacitors in the implanted heart pacemaker pulse generator canister 164. It is noted that other external power sources can be used to power the charging/voltage source in the implanted heart pacemaker pulse generator canister 164.

Figure 4:
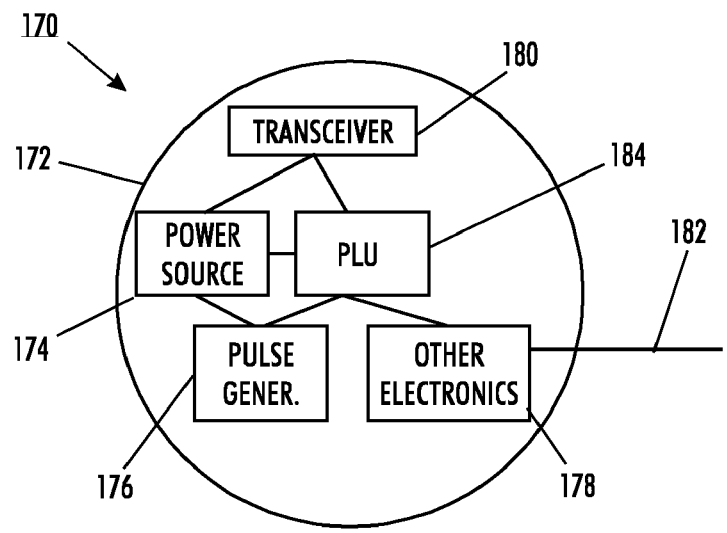
FIG. 4 illustrates an embodiment of a pacemaker canister according to the concepts of the present invention.

FIG. 4 is a diagram of an assembly 170 for the pacemaker generator components comprising the canister housing 172, a programmable logic unit (PLU) 184, a power source 174, and a pulse generator 176. Additionally, means for communicating with an external sensor/transceiver is provided by transceiver 180. Other electronic components 178; e.g., signal filters, signal processors, lead connectors, etc. are also located in the canister 172. The pacing leads 182 pass through the canister 172 and connect to the internal electronics 178. During a magnetic resonance imaging examination, the signals transmitted and received by the transceiver 180 may be used to synchronize the magnetic resonance imaging system's scanning sequences with the delivery of the pacing signals.

Figure 5:
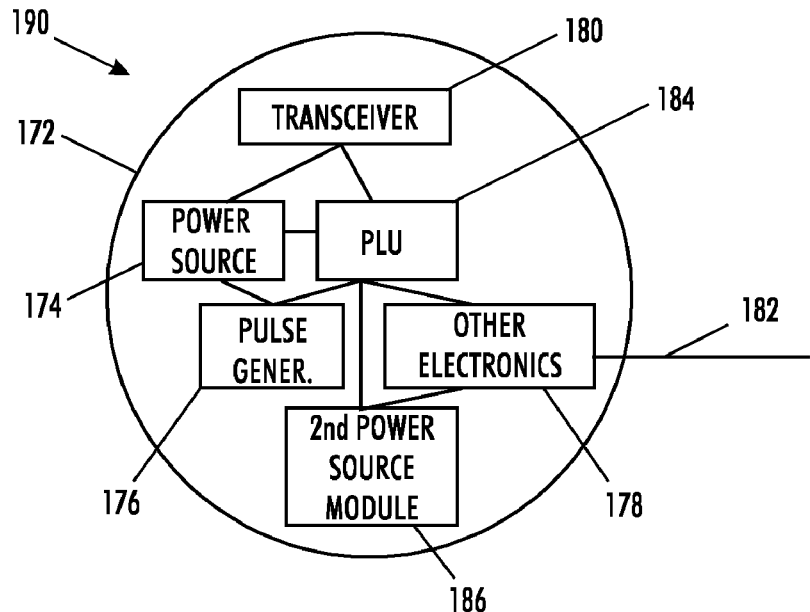
FIG. 5 illustrates another embodiment of a pacemaker canister according to the concepts of the present invention.

In another embodiment, as depicted in FIG. 5, the pacing generator assembly 190 further includes a second power module 186 which may be an inductive coil and/or capacitor bank, suitable for capturing and storing power from the magnetic resonance imaging system's transmitted radio-frequency signal.

In one embodiment, the power stored in the power module 186 is used to develop an electrical potential in the leads 182 that is opposed to that which is induced by the application of the magnetic resonance imaging system's gradient fields.

In another embodiment, the power stored in the power module 186 is used to operate various switches in the electronics module 178 which may switch in or out various power serge protection circuits in-line and/or signal filters to the leads 182.

In a further embodiment, and referring to FIG. 5, the module 186 may be used to electrically charge the pacemaker canister 172, which is made of a conductive material, in synchronization with the application of the magnetic resonance imaging system's gradient fields so that the electrical potential difference between the pacing electrodes and the pacemaker canister 172 is reduced. That is, the sum of the induced voltage difference due to the application of the gradient fields plus the voltage difference due to the application of the electrical charge stored in the power module 186 results is a net voltage significantly below any threshold level, above which a problem may develop.

Figure 6:
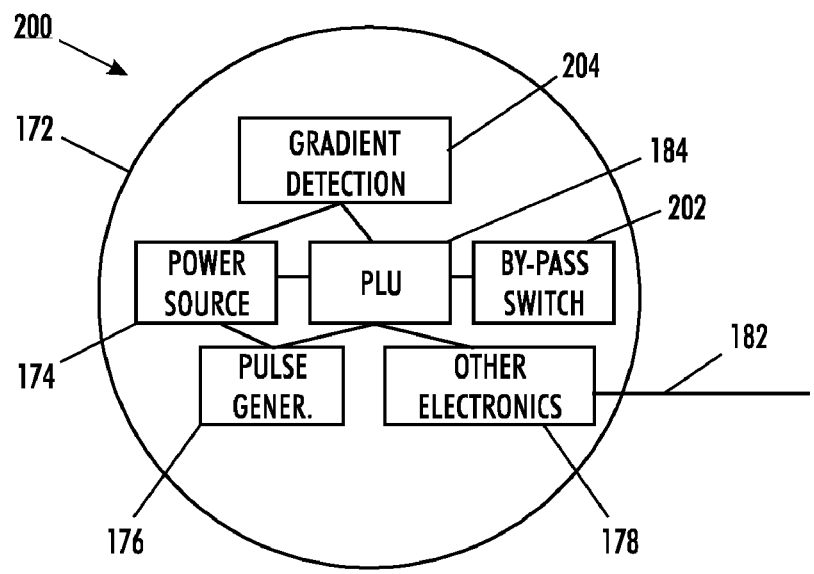
FIG. 6 illustrates a further embodiment of a pacemaker canister according to the concepts of the present invention.

FIG. 6 depicts another assembly 200, which includes the basic components of FIG. 5 less the transceiver 180, a gradient field detector 204, and a by-pass switch component 202. By detecting the gradient signal in the pacemaker canister 172 with gradient field detector 204, the pacemaker can switch filters and/or other electronics 178 in or out of the circuit.

In one embodiment, when no gradient fields are detected, the switch 202 is closed to by-pass the electronics component 178, which may be a combination of low-pass, high-pass, notch filters, diodes, and/or other electronics. In this mode (switched closed), the pacing pulse (and sensing signals) by-pass the filters components 178. When gradient field detector 204 detects the gradient signals, the switch 202 is opened and any gradient fields induced signals in the leads 182 are blocked or significantly reduced by the filters components 178. In the open mode, the pacing and sensing signals pass through the filters component 178 as well.

The gradient detector 204 may communicate the sensing of the gradient field to other components in the pacemaker via its connection to the PLU 184 so that the pacing signal can be modified, if necessary, to compensate for any distortion it may suffer by now going through the filters component 178. Additionally, the sensing signal, now also passing through the filter components 178 may be distorted. This may be compensated for by including signal recovery/reconstruction logic into the PLU or into a separate signal-processing component.

Referring back to FIG. 1, by increasing the impedance of the leads 104, the voltage across the tissue gap or spacing from the electrodes 112 and the pacemaker canister 102 can be reduced. Inserting a resistor or using a higher resistive wire for the pacemaker leads 104 will reduce the current induced in the current loop, which includes the virtual loop portion across the (heart 112) tissue to the pacemaker generator canister 102.

By using various inductors in-line with the various leads 104, it is possible to make the leads 104 have high impedance for the low frequency magnetic resonance imaging gradient fields' frequency and low impedance for the magnetic resonance imaging system's radio-frequency frequency. Alternatively, different impedances (inductors/resistors/capacitors) may be switched in-line or out of the leads' circuitry depending on the timing and application of the gradient and/or radio-frequency fields.

In another embodiment, not shown, the pacemakers' electronics can be augmented to include one or more digital signal processors. By converting the sensing signal into a digital signal, the digital signal processor (DSP) can reconstruct the sensing signal after it has passed through filters and has been distorted by the filtering or other elements that may have been added to the lead circuit. The DSP may also be used to reject any signals that do not have a correct cardiac signature, thus rejecting any signals caused by the switched gradient fields, which is a non-cardiac signal.

In another embodiment of the present invention, a pacemaker lead or other medical device, having a long conductive lead and functioning in a magnetic resonance imaging environment, may be configured, according to the concepts of the present invention, to include additional loops to cancel the induced voltage effects in the leads of the original current loop formed by the leads.

Figure 7:
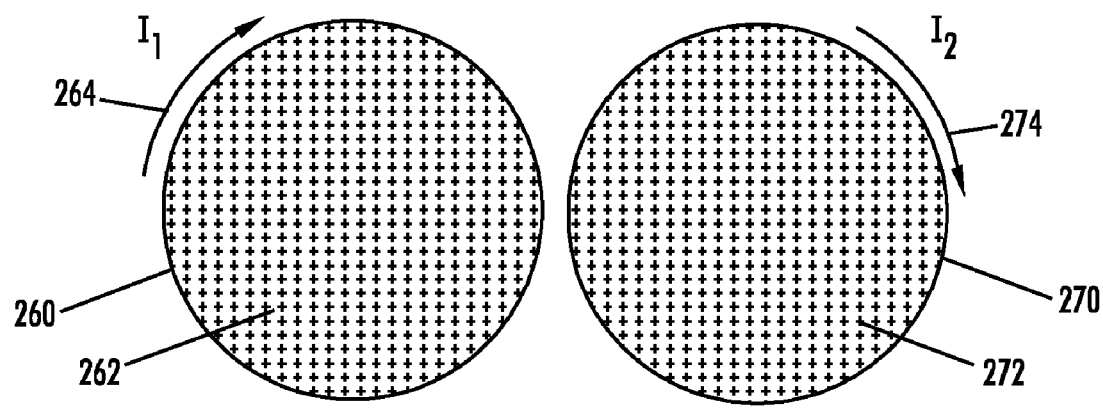
FIG. 7 is an illustration of inductive currents in conductor loops.

In FIG. 7, two conductive loops 260 and 270 having the same amount of area and in the same plane, positioned in a changing magnetic field 262 and 272, develop currents 264 and 274. In FIG. 7, both induced currents $I_1$ and $I_2$ travel in the same direction (clockwise direction shown) at all times as the magnetic field 262 and 272 oscillate.

Figure 8:
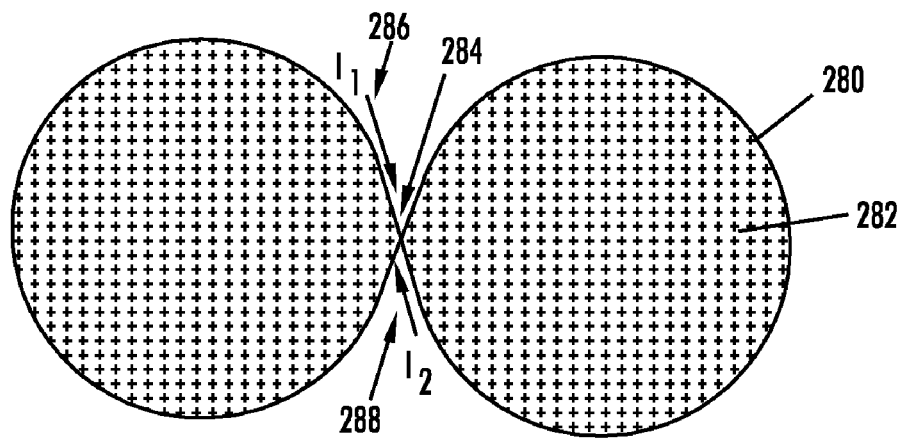
FIG. 8 is an illustration of canceling inductive currents in conductor loops according to the concepts of the present invention.

FIG. 8 shows that by connecting the two conductive loops 260 and 270 of FIG. 7 to form a single conductor 280, the currents induced in each lobe can be made to cancel each other out. The two loops are connected so that a single conductor is formed which crosses over itself at 284. In this case, as shown in FIG. 8, the two currents 286 and 288 cancel each other out resulting in net current of zero magnitude around the conductor 280. This type of configuration of conductors in a changing magnetic field may be used to cancel induced currents in the conductors.

Figure 9:
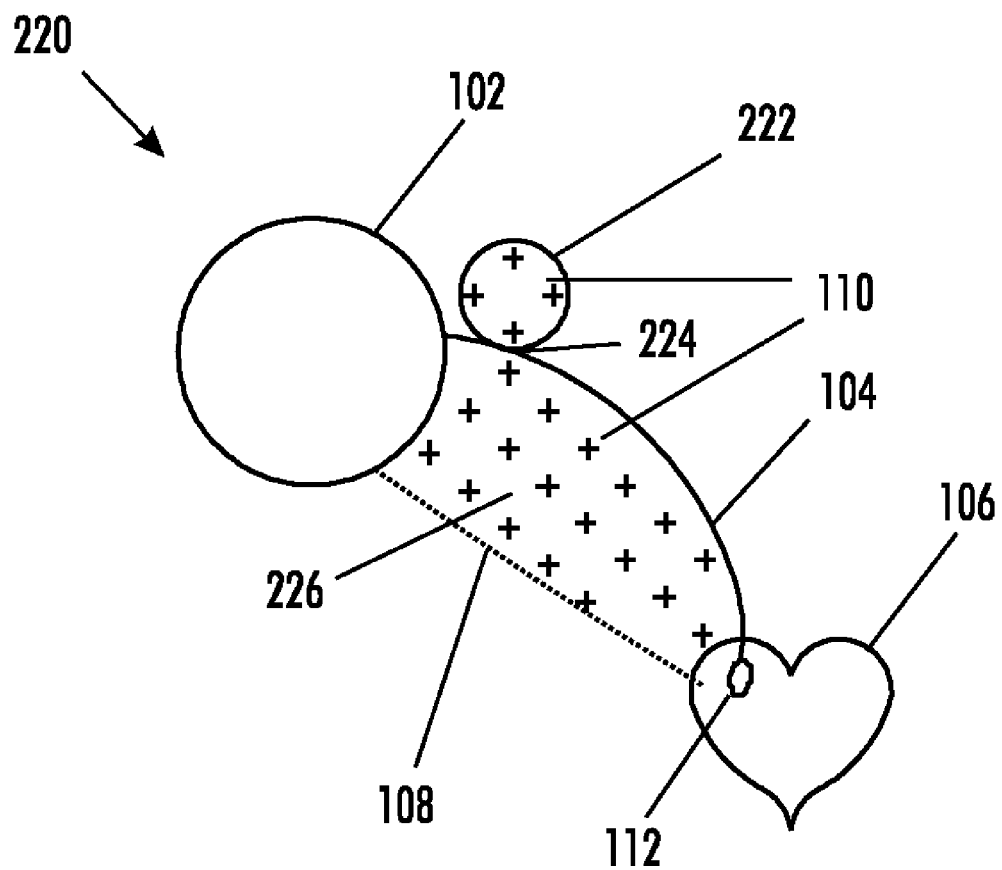
FIG. 9 is a schematic of an embodiment of a pacemaker lead utilizing inductive loops according to the concepts of the present invention.

FIG. 9 depicts an implanted pacemaker system 220 comprising a pacing generator canister 102, conductive leads 104, and electrodes 112 positioned in the heart 106. Additional loops 222 are added to the overall configuration of the lead 104 in the body with one or more crossings 224. In accordance with the concepts of the present invention, the plane of the loop 222 is in the same plane as defined by the rest of the lead geometry.

The same oscillating magnetic field 110 passes through loop 222 and the loop defined by generator canister 102, conductive leads 104, electrodes 112, and conductive path 108 through the body from the heart 106 to the generator canister 102. It is noted that the total area enclosed by the loops can be adjusted by adding or removing loops 222 or by changing the area enclosed by the loops (singly or collectively).

In one embodiment, the total area of the loop 222 is the same as the loop area 226. In another embodiment, the total area of the loop 222 is different from loop area 226. In another embodiment, the plane of loop 222 is different from the plane of loop area 226. In yet another embodiment, loop 222 and/or loop area 226 do not define a single plane but are curved in three different spatial directions. In yet another embodiment, loop 222 consists of at least three loops in three orthogonal planes.

In a further embodiment (not shown), new additional loops can be positioned in such a way as to encircle the pacemaker's generator canister. In another embodiment (not shown), the additional loops may be positioned inside the pacemaker's generator canister.

Referring back to FIG. 9, a fastener (not shown) can be used at the loop cross over point 224 to allow for adjustment of the loop's enclosed area and/or orientation and, once adjusted, to lock in the loop's adjustments. This same fastener can also be used to adjust a plurality of loops.

In a further embodiment of FIG. 9, pacemaker's generator canister 102 may include an orientation subsystem for automatically changing a spatial orientation of the coil to modify the strength of the magnetic resonance imaging switched gradient field induced current. In this embodiment, the orientation subsystem may sense the magnitude of the magnetic resonance imaging switched gradient field induced current (voltage) and spatially tune the orientation of the coils so as to produce more current to oppose the magnetic resonance imaging switched gradient field induced current or less current to oppose the magnetic resonance imaging switched gradient field induced current based upon the sensed magnitude of the magnetic resonance imaging switched gradient field induced current (voltage).

In other words, if greater current is needed to oppose the magnetic resonance imaging switched gradient field induced current, the orientation subsystem would spatially move or adjust one or more coils such that their surface planes become more perpendicular to the magnetic resonance imaging gradient field lines, thereby inducing a greater magnitude of current to oppose the magnetic resonance imaging switched gradient field induced current. On the other hand, if less current is needed to oppose the magnetic resonance imaging switched gradient field induced current, the orientation subsystem would spatially move or adjust one or more coils such that their surface planes become less perpendicular and more parallel to the magnetic resonance imaging gradient field lines, thereby inducing a lesser magnitude of current to oppose the magnetic resonance imaging switched gradient field induced current.

In another aspect of the present invention, a selection mechanism can be included in the pacemaker system. This selection mechanism is used to adjust the number of loops to include in the circuit.

For example, if the loops are located within the pacemaker canister, the selection mechanism can be used to manually select how many loops to include in the lead circuit depending on where the pacemaker can is placed in the body and the length of the lead. Alternatively, the selection mechanism may be used to automatically select how many loops to include in the lead circuit depending on where the pacemaker can is placed in the body and the length of the lead. In this alternative embodiment, the present invention monitors the voltages on the pacemaker's lead(s) and selects a different number of loops to connect to the lead(s) to cancel any induced voltages. Lastly, the selection mechanism may be externally programmed and transmitted to the pacemaker's PLU that then monitors and adjusts the number of loops in the lead circuit.

Figure 10:
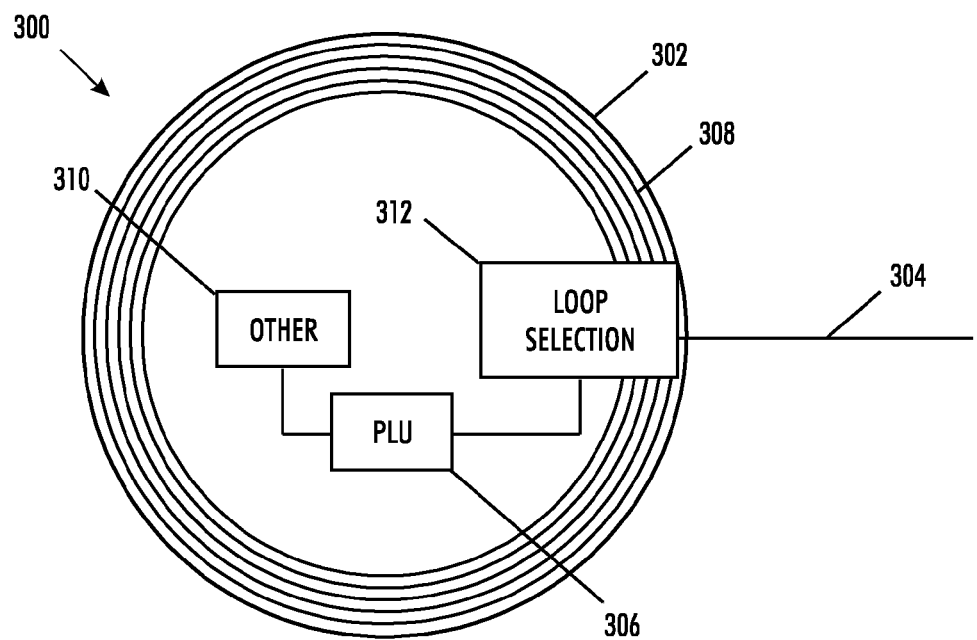
FIG. 10 is a schematic of an embodiment of inductive loops in a pacemaker canister according to the concepts of the present invention.

FIG. 10 is a schematic of a pacemaker system 300 that includes a pacemaker canister 302 and the pacemaker's leads 304. The pacemaker's canister 302 contains a programmable logic unit (PLU) 306, and other electronics 310, e.g. a pulse generator, power supply, etc. The system 300 further includes conductive loops 308 positioned within the pacemaker canister 302.

The conductive loops are connected to a loop selection component 312 that provides means for selectively adjusting the number of loops to be included in the leads' circuit 304. The leads 304 are also connected to the loop selection component 312 so that the leads 304 can be electrically connected to the loops 308.

The loop selection component 312 connects the loops 308 to the leads' circuit 304 in such a way that any induced voltages in the loops 308 caused by changing magnetic fields in the environment, e.g. an magnetic resonance imaging environment, will cancel out or significantly reduce in magnitude any induced voltage along the leads 304 that have also been caused by the environment's changing magnetic fields.

In one embodiment, the loop selection component 312 is adjusted manually by screws, connection pins, and/or other means.

In another embodiment, the loop selection component 312 is controlled by the PLU 306. The PLU 306 may include means for receiving loop selection instructions from an external transmitter or may include sensors that measure environmental variables, e.g. changing magnetic fields in a magnetic resonance imaging environment. From this information, the PLU 306 dynamically adjusts the loop selection component's 312 adjustable parameters so as to change which loops are included in the leads' circuitry 304. It is noted that the loops 308 need not be all in the same plane.

In a further embodiment of FIG. 10, pacemaker's generator canister 302 may include an orientation subsystem for automatically changing a spatial orientation of the coil to modify the strength of the magnetic resonance imaging switched gradient field induced current. In this embodiment, the orientation subsystem may sense the magnitude of the magnetic resonance imaging switched gradient field induced current (voltage) and spatially tune the orientation of the coils so as to produce more current to oppose the magnetic resonance imaging switched gradient field induced current or less current to oppose the magnetic resonance imaging switched gradient field induced current based upon the sensed magnitude of the magnetic resonance imaging switched gradient field induced current (voltage).

In other words, if greater current is needed to oppose the magnetic resonance imaging switched gradient field induced current, the orientation subsystem would spatially move or adjust one or more coils such that their surface planes become more perpendicular to the magnetic resonance imaging gradient field lines, thereby inducing a greater magnitude of current to oppose the magnetic resonance imaging switched gradient field induced current. On the other hand, if less current is needed to oppose the magnetic resonance imaging switched gradient field induced current, the orientation subsystem would spatially move or adjust one or more coils such that their surface planes become less perpendicular and more parallel to the magnetic resonance imaging gradient field lines, thereby inducing a lesser magnitude of current to oppose the magnetic resonance imaging switched gradient field induced current.

Figure 11:
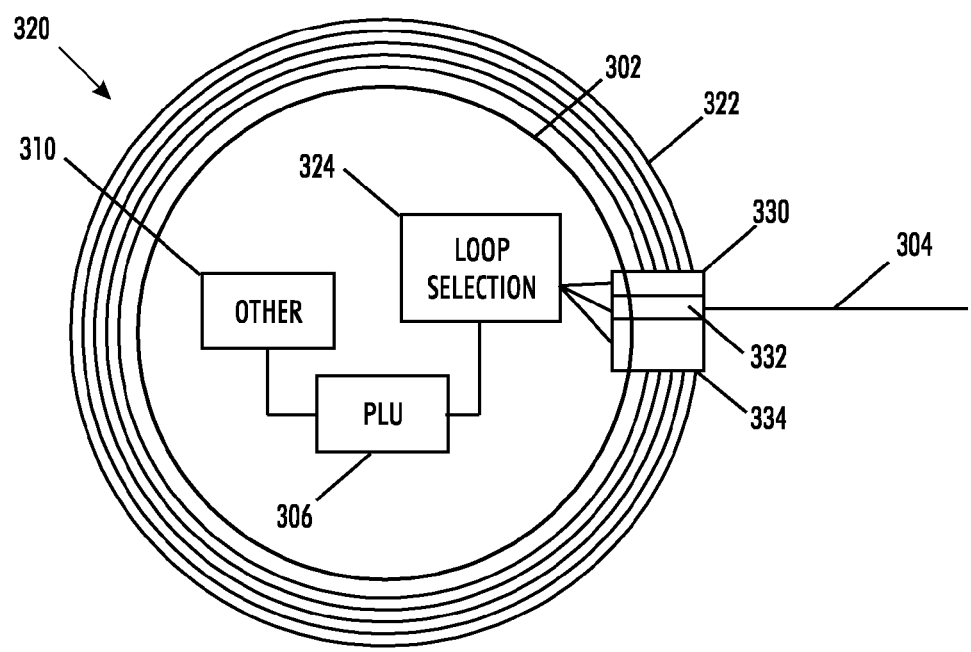
FIG. 11 is a schematic of an embodiment of inductive loops with a pacemaker canister according to the concepts of the present invention.

FIG. 11 is a schematic of another pacemaker system 320. Pacemaker system 320 includes conductive loops 322 positioned externally to a pacemaker canister 302. In this embodiment, the loops 332 are connected to an input port connection 330 and to an output port connection 334 which are electrically connected to the loop selection component 324 located inside the pacemaker canister 302. Additionally, the pacemaker leads 304 are connected to an electrical connector 332 that is electrically connected to the loop selection component 324. It is noted that the conductive loops 322 need not be all in the same plane.

In a further embodiment of FIG. 11, pacemaker system 320 may include an orientation subsystem for automatically changing a spatial orientation of the coil to modify the strength of the magnetic resonance imaging switched gradient field induced current. In this embodiment, the orientation subsystem may sense the magnitude of the magnetic resonance imaging switched gradient field induced current (voltage) and spatially tune the orientation of the coils so as to produce more current to oppose the magnetic resonance imaging switched gradient field induced current or less current to oppose the magnetic resonance imaging switched gradient field induced current based upon the sensed magnitude of the magnetic resonance imaging switched gradient field induced current (voltage).

In other words, if greater current is needed to oppose the magnetic resonance imaging switched gradient field induced current, the orientation subsystem would spatially move or adjust one or more coils such that their surface planes become more perpendicular to the magnetic resonance imaging gradient field lines, thereby inducing a greater magnitude of current to oppose the magnetic resonance imaging switched gradient field induced current. On the other hand, if less current is needed to oppose the magnetic resonance imaging switched gradient field induced current, the orientation subsystem would spatially move or adjust one or more coils such that their surface planes become less perpendicular and more parallel to the magnetic resonance imaging gradient field lines, thereby inducing a lesser magnitude of current to oppose the magnetic resonance imaging switched gradient field induced current.

Figure 12:
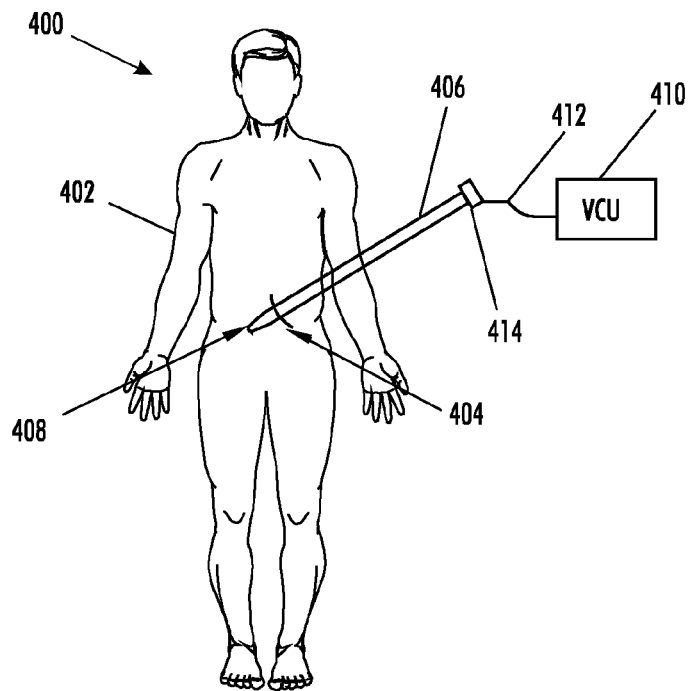
FIG. 12 illustrates of an embodiment of a medical device with an external voltage cancellation unit according to the concepts of the present invention.

FIG. 12 depicts a medical procedure in which a catheter 406 or other medical device, e.g. a guidewire, which is comprised of conductive leads or other conductive components, may be partially inserted into a body 402 and partially external to the body. In an magnetic resonance imaging environment, such conductive medical devices 406 can develop problems like heating, induced voltages, etc. caused by the changing magnetic fields of the magnetic resonance imaging system. To compensate for induced currents and/or induced voltages in such devices 406, a voltage compensation unit (VCU) 410 is electrically connected to the medical device 406 via conductive leads 412 and electrical connectors 414, externally to the patient's body 402.

The medical device 406 is constructed with additional electrical connectors 414 to allow for easy attachment of the VCU device 410. The VCU device 410 is connected to a power supply or may have a built in power supply, e.g. batteries. The VCU device 410 has sensors built into it, which monitor the voltages of the conductive components in the medical device 406, and delivers opposing voltages to the medical device 406 to cancel out or significantly reduce any induced voltages caused by the changing magnetic fields in an magnetic resonance imaging (or other) environment.

Additionally or alternatively, the VCU device 410 has sensors to detect the changing magnetic fields of the magnetic resonance imaging system and can synchronize the application of the canceling voltage with the magnetic resonance imaging system's changing fields.

Figure 13:
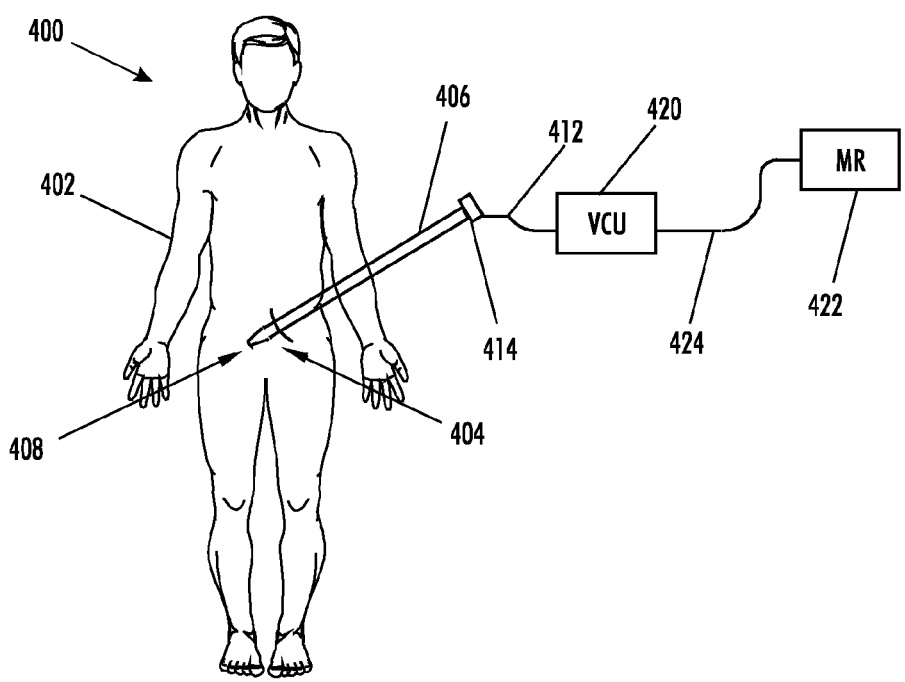
FIG. 13 illustrates of another embodiment of a medical device with an external voltage cancellation unit according to the concepts of the present invention.

In another embodiment depicted in FIG. 13, the VCU device 420 is connected to the magnetic resonance imaging system 422 via communication means 424 so that the start and end of the application of the magnetic resonance imaging system's 422 fields may be communicated to the VCU device 420. Other information that may be required (field strengths to be applied, magnetic resonance imaging scan sequence, etc.) may also be communicated to the VCU device 420. The communication means 424 may be electrical wires/coaxial/shielded/other, optical fiber, or a radio-frequency transmitter/receiver, or some sonic means of communication.

The conductive lead of a heart pacemaker is a filer winding. The filer winding may consist of two or more conductive stands coiled together in a spring-like configuration. The current (pulses, signals) then flows over the surface and through the contact points between one loop and the adjacent loop of the winding, rather than following the windings of the individual conductive strands. This occurs because there is no significant insulating material or surface coating between the contact points of the windings.

In accordance with the present invention, to reduce the alternating, induced current flowing, caused by a magnetic resonance system's changing magnetic fields, through the for example, pacemaker's winding leads, the inductance value of the pacemaker's lead may be changed to increase the overall impedance of the pacemaker's lead.

Thus in one embodiment, a suitable radio-frequency choke is inserted inline with the pacemaker's lead, preferable near the distal tip. For example, referring back to FIG. 2 and to the embodiment therein, electronic component 146 and/or 144 may comprise a radio-frequency choke. In a preferred embodiment, the radio-frequency choke has an inductance value of about 10 microHenries. In another embodiment, the inductance value is about 2 microHenries.

The specific value of inductance to introduce into the, for example, pacemaker's lead depends in part on the frequency of the induced signal from the magnetic resonance imaging system's imaging sequence that is to be blocked or significantly reduced.

Figure 14:
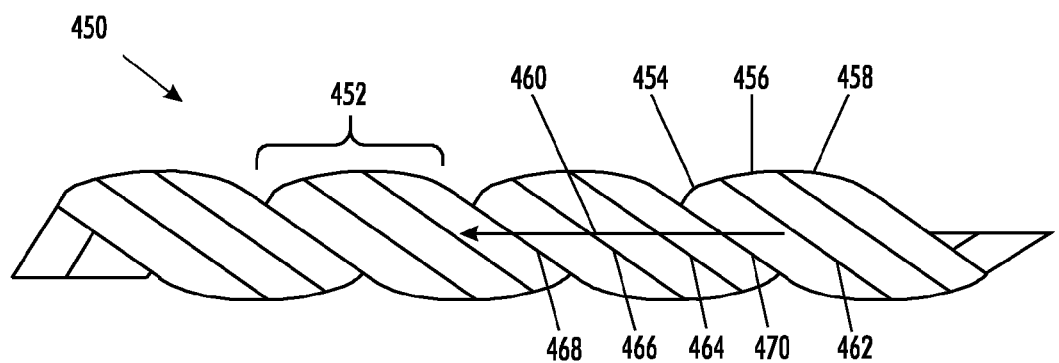
FIG. 14 illustrates a portion of coiled leads used in a medial device according to the concepts of the present invention.

FIG. 14 shows a portion of a coiled multi-filer lead 450. As illustrated in FIG. 14, lead 450 includes a plurality of coil loops 452; each coil loop 452 consists of three conductive strands 454, 456, and 458. A current 460 through the lead 450 can cross contact points 464, 466, and 462 between the strands as well as the coil contact points 468 and 470. Thus, the current 460 does not necessarily follow the coiling of the lead's conductive strands 454, 456, and 458.

Figure 15:
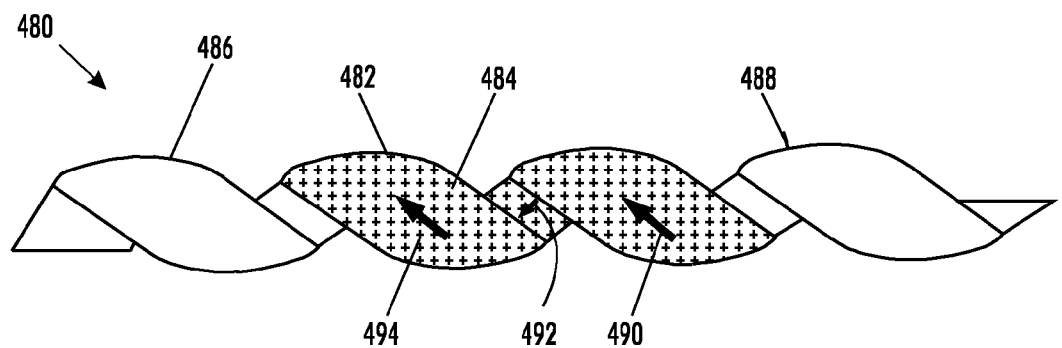
FIG. 15 illustrates another embodiment of a portion of coiled leads used in a medial device according to the concepts of the present invention.

FIG. 15 shows a portion of a coiled lead assembly 480 including a region 482 that has an insulating coating 484 applied to its surface. The coiled lead assembly 480 is depicted in an elongated position in which adjacent coil windings are not in contact with one another. It is to be understood that the normal, relaxed position of the lead assembly 480 has all adjacent coiled windings in contact.

With the addition of an insulated coating 484 over the winding region 482, the current 490, 492, and 494 is now forced to substantially follow the curvature of the coiled winding 482, thus forming an inductive coil inline with the conductive lead regions 486 and 488 which do not have an insulated coating. The inductive value of the created inductor can be adjusted by adjusting the length of the region to which the insulative coating 484 is applied.

It is noted that the coating 484 may be a partially resistive material. In such an example, the inductance is then adjusted by adjusting the resistive properties of the material 484.

Figure 16:
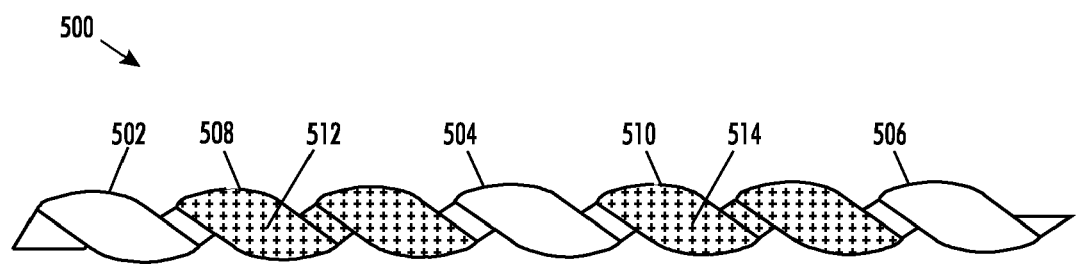
FIG. 16 illustrates a further embodiment of a portion of coiled leads used in a medial device according to the concepts of the present invention.

FIG. 16 is a schematic of a coiled lead assembly 500 comprised of uninsulated regions 502, 504, and 506, and coated insulated regions 508 and 510 with coatings 512, and 514, respectively. Through the application of the coating, the current is forced to substantially follow the curvature of the coiled windings, thus forming an inductive coil inline with the conductive lead regions that do not have a coating applied thereto. The inductive value of the created inductor can be adjusted by adjusting the length of the region to which the insulative coatings 512 and 514 are applied. In one embodiment, coatings 512 and 514 are the same coatings. In another embodiment, the coatings 512 and 514 are different materials.

It is noted that coatings 512 and 514 may be the same coating material but having differing properties, e.g., the thickness of the coatings, or the length of the coated region 508 and 510. It is further noted that the two-coated regions 508 and 510 may have different inductive values. It is also noted that more than two different regions along the length of the lead assembly can be coated.

Figure 17:
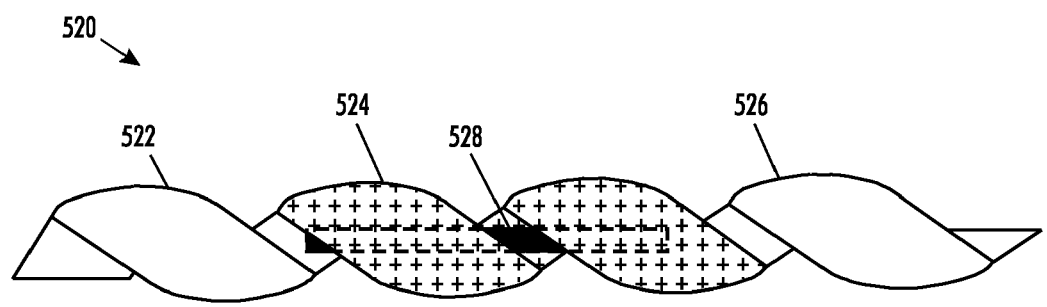
FIG. 17 illustrates another embodiment of a portion of coiled leads used in a medial device according to the concepts of the present invention.

FIG. 17 is a schematic of a portion of a coiled lead assembly 520 including at least one region 524 with a coating applied thereto. Through the application of the coating, the current is forced to substantially follow the curvature of the coiled windings, thus forming an inductive coil inline with the conductive lead regions 522 and 526 that do not have a coating applied thereto. The inductive value of the created inductor can be adjusted by adjusting the length of the region to which the insulative coating 524 is applied. Additionally, through the coated region 524 is positioned a rod 528 which also changes the inductive value of the coated region 524. It is noted that the rod 528 may be of ferrite material. It is further noted that multiple rods can be inserted into multiple coated regions along the length of the coiled lead.

It is noted that multiple coatings can be applied to the same coated region of the coiled lead wherein the multiple coating layers may be comprised of different materials. It is further noted that one or more layers of the multiple layers of coatings may comprise ferrite material.

In another embodiment of the present invention, the heating and/or induced voltages on catheters or guide wires is controlled or substantially eliminated by introducing or creating detuned characteristic impedance at a proximal ends (ends that are not within the body) of the catheters or guide wires. This introduction or creation of detuned characteristic impedance will be discussed in more detail with respect to FIGS. 18-21.

As noted above, during magnetic resonance imaging procedures, catheters and guide wires (wire lines), with or without grounded shielding, are used to measure physiological signals. In such instances, two-wire catheters or guide wires having a grounded shield have one conductor that carries the actual measured signal and the other wire is grounded. In terms of characteristic impedance, the two-wire catheters or guide wires having a grounded shield are unbalanced. In contrast, a single wire catheter or guide wire has characteristic impedance that is balanced.

According to the concepts of the present invention, the characteristic impedance of the catheters and guide wires, used during magnetic resonance imaging procedures, should be unbalanced at the proximal end, under all conditions, to reduce or eliminate heating and induced voltages. To realize this reduction or elimination of heating and induced voltages at the proximal end of the catheters and guide wires, used during magnetic resonance imaging procedures, by creating an unbalanced characteristic impedance, the present invention proposes providing a Balun along the catheter and/or guide wire or at the proximal end of the catheter and/or guide wire.

Using a Balun to maintain unbalanced characteristic impedance, the reactance at the distal end of the catheter and/or guide wire approaches infinity. Thus, even when there is some potential on the wire, the unbalanced characteristic impedance has approximately four times the ground loop looses of a balanced line, thereby substantially avoiding any incident of thermal injury. An example of such an arrangement is illustrated in FIG. 18.

Figure 18:
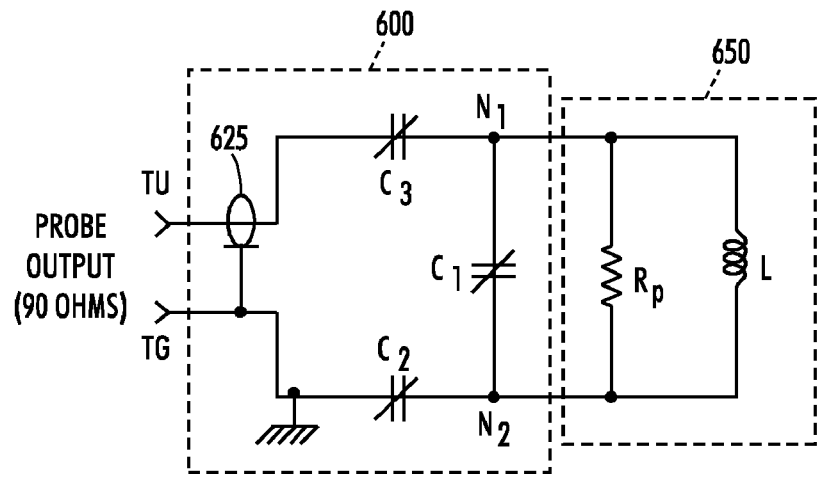
FIG. 18 illustrates a circuit diagram representing a guide wire with an unbalancing impedance circuit according to the concepts of the present invention.

As illustrated in FIG. 18, a guide wire or catheter 650 has characteristic impedance due to its intrinsic resistance from intrinsic resistor capacitors $R_P$ and its intrinsic inductance from intrinsic inductor L. To create the unbalanced characteristic impedance at the proximal end of the guide wire or catheter 650, a Balun 600 is placed along the guide wire or catheter 650. In other words, the Balun 600 is in vitro.

The Balun 600 includes a variable capacitor $C_1$ connected in parallel with the guide wire or catheter 650 and two variable capacitors $C_2$ and $C_3$ connected in series with the guide wire or catheter 650. It is noted that one end of the variable capacitor $C_2$ is connected to the shield 625 and ground or a known voltage. The capacitance of the variable capacitors $C_1$, $C_2$, and $C_3$ are adjusted to create the unbalanced characteristic impedance.

More specifically, the variable capacitors $C_1$, $C_2$, and $C_3$ may be used for both matching and providing a certain amount of balancing for the guide wire or catheter 650 characteristic impedance. In this example, the variable capacitors $C_1$, $C_2$, and $C_3$ lift the voltage on the guide wire or catheter 650 from ground. The larger the reactance of the variable capacitors $C_1$, $C_2$, and $C_3$, the more symmetric and balanced the circuit of the guide wire or catheter 650 becomes. Conversely, according to the concepts of the present invention, if the reactive capacitance of the Balun 600 is detuned (made less resonant), the circuit of the guide wire or catheter 650 becomes asymmetric and unbalanced, breaking down, to reduce the chances of thermal injury at the distal end of the guide wire or catheter 650 due to heating from induced voltages.

Figure 19:
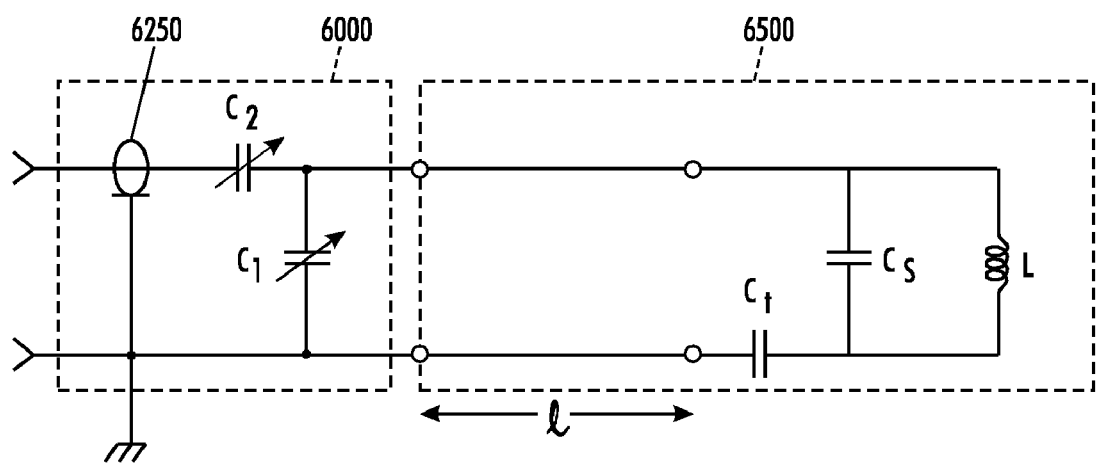
FIG. 19 illustrates another embodiment of a circuit diagram representing a guide wire with an unbalancing impedance circuit according to the concepts of the present invention.

FIG. 19 illustrates another embodiment of the present invention wherein a guide wire or catheter 6500 has characteristic impedance due to its intrinsic capacitance from intrinsic capacitors $C_t$ and $C_s$ and its intrinsic inductance from intrinsic inductor L. To create the unbalanced characteristic impedance at the proximal end of the guide wire or catheter 6500, a Balun 6000 is connected across the proximal end of the guide wire or catheter 6500. In other words, the Balun 6000 is outside the body at the proximal end of the guide wire or catheter 650. By having the Balun 6000 outside the body, the varying of the reactance of the guide wire or catheter 6500 can be readily and manually controlled.

The Balun 6000 includes a variable capacitor $C_1$ connected in parallel with the guide wire or catheter 6500 and a variable capacitor $C_2$ connected in series with the guide wire or catheter 6500. It is noted that one end of the variable capacitor $C_1$ is connected to the shield 6250 and ground or a known voltage. The capacitance of the variable capacitors $C_1$ and $C_2$ are adjusted to create the unbalanced characteristic impedance.

More specifically, the variable capacitors $C_1$, and $C_2$ may be used for both matching and providing a certain amount of balancing for the guide wire or catheter 6500 characteristic impedance. In this example, the variable capacitors $C_1$, $C_2$, and $C_3$ lift the voltage on the guide wire or catheter 6500 from ground. The larger the reactance of the variable capacitors $C_1$ and $C_2$, the more symmetric and balanced the circuit of the guide wire or catheter 6500 becomes. Conversely, according to the concepts of the present invention, if the reactive capacitance of the Balun 6000 is detuned (made less resonant), the circuit of the guide wire or catheter 6500 becomes asymmetric and unbalanced, breaking down, to reduce the chances of thermal injury at the distal end of the guide wire or catheter 6500 due to heating from induced voltages.

Figure 20:
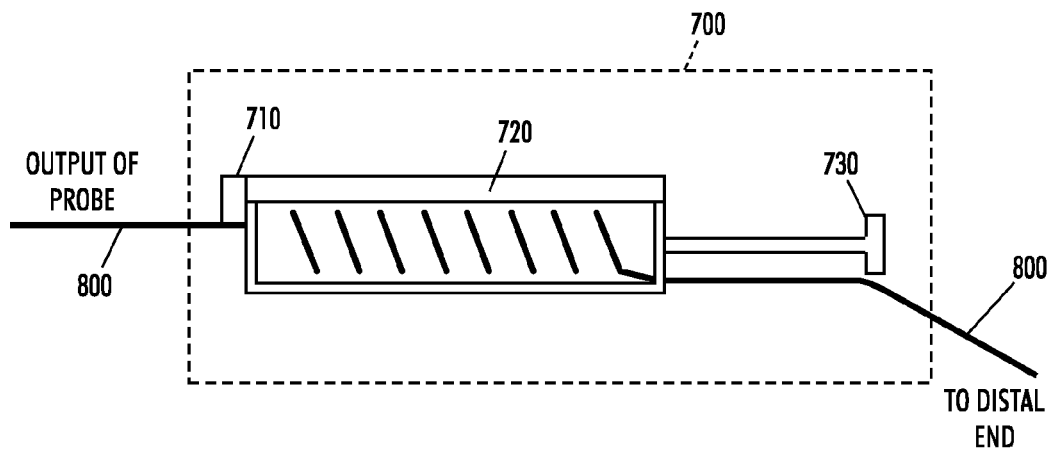
FIG. 20 illustrates a balun used in conjunction with a guide wire according to the concepts of the present invention.

FIG. 20 illustrates a further embodiment of the present invention wherein a guide wire or catheter 800 is connected to a Balun 700. The Balun 700 includes a variable capacitor 710, a copper foil 720, and a non-conductive tuning bolt 730. The Balun 700 is further connected to the output of the probe 800

The Balun 700 adjusts its characteristic impedance by increasing or decreasing the number wire coils are found within the copper foil 720. The combination of the coils and the copper foil 720 forms a variable capacitor, having it impedance determined by the change in the surface area of the coils positioned opposite of the copper foil 720. As more coils are introduced into the volume created by the copper foil 720, the capacitance of this combination increases. Moreover, as fewer coils are introduced into the volume created by the copper foil 720, the capacitance of this combination decreases. Thus, the capacitance of the Balun 700 is adjusted to create the unbalanced characteristic impedance.

Figure 21:
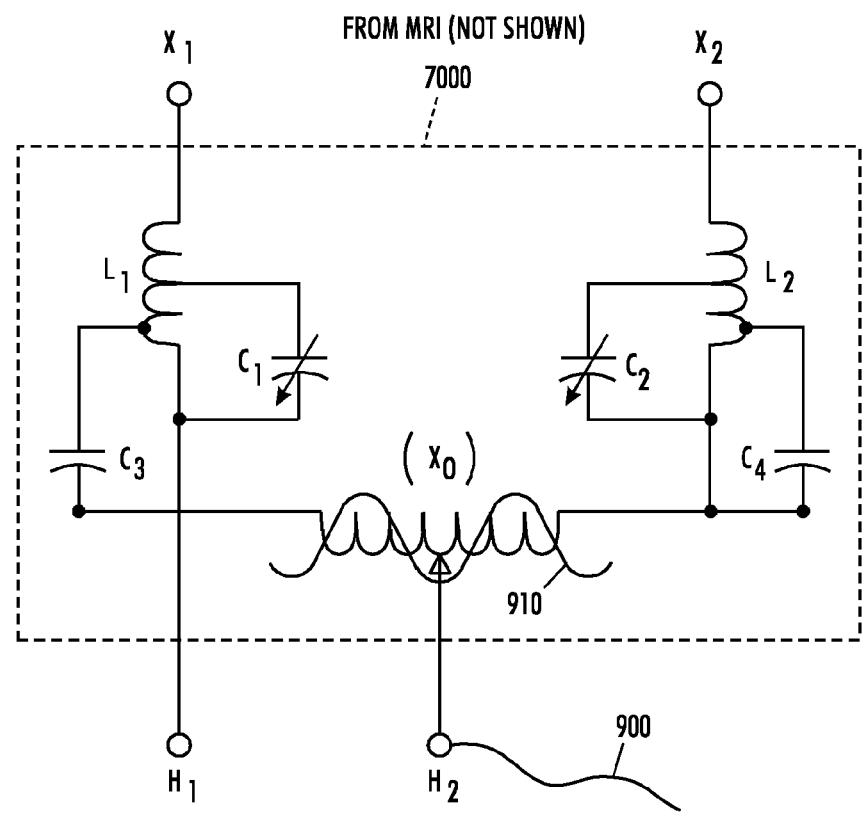
FIG. 21 is a circuit diagram representing a capacitance unbalanced balun unit according to the concepts of the present invention.

FIG. 21 illustrates another embodiment of the present invention wherein a guide wire or catheter 900 is electronically isolated by a voltage control unit to always appear as an unbalanced line to any possible magnetic field that may be applied from a magnetic resonance imager unit (not shown). As current begins to flow due to the changing magnetic fields from the magnetic resonance imaging, a tapped voltage from a voltage-controlled oscillator in the magnetic resonance imaging unit is applied across terminals X1 and X2 of the voltage control unit.

According to the concepts of the present invention, to automatically maintain an unbalanced characteristic impedance at the distal end of the guide wire or catheter 900, a capacitance unbalanced balun unit 7000, located within the voltage control unit, is connected through a variable inductor 910 to the proximal end of the guide wire or catheter 900. In other words, the voltage control unit containing the capacitance unbalanced balun unit 7000 is outside the body at the proximal end of the guide wire or catheter 900. By having the capacitance unbalanced balun unit 7000 and variable inductor 910 outside the body, the varying of the reactance (X0) of the guide wire or catheter 900 can be readily adjusted and automatically controlled by the voltage control unit circuit's reactance to the tapped voltage from the voltage-controlled oscillator in the magnetic resonance imaging unit as it is applied across X1 and X2 for any instance of time from time zero (T0) or instantiation of the magnetic resonance imaging radio-frequency pulses.

The capacitance unbalanced balun unit 7000 includes two non-magnetic trimmer capacitors C1 and C2 connected in parallel with LC circuits (L1, C3) and (L2, C4), respectively, setting up a simplified dual T network that is effectively in series with the guide wire or catheter 900. It is noted that one end of the simplified dual T network is connected to neutral H1 and the other end is connected to a continuously variable voltage H2, based on inputs to the circuit from the voltage-controlled oscillator in the magnetic resonance imaging unit at X1 and X2. The reactance (X0) of the LC circuits in the T network is automatically adjusted to create the desired unbalanced characteristic impedance.

More specifically, the T network L1, C1, C3 and L2, C2, C4 respectively, may be used for both matching and unmatching characteristic impedance of the guide wire or catheter 900 and to provide a certain amount of balancing or unbalancing for the guide wire or catheter 900 by varying the circuit's capacitive or inductive reactance (X0).

In this example, as the voltage from the voltage-controlled oscillator in the magnetic resonance imaging unit is provided to the voltage control unit (X1 and X2), the two non-magnetic trimmer capacitors C1 and C2, connected in parallel with LC circuits, (L1, C3) and (L2, C4), lift the voltage on the guide wire or catheter 900 from ground to an unbalanced state with respect to the radio-frequency pulse applied by the magnetic resonance imaging unit. The reactance of the T network and its LC circuits, (L1, C3) and (L2, C4), respectively, cause the guide wire or catheter 900 to become asymmetric and unbalanced, automatically breaking down the reactance to ensure that resonance for the guide wire or catheter 900 is never present, thus reducing the chances of thermal injury at the distal end of the guide wire or catheter 900 due to heating from induced voltages.

In the following descriptions, the term, "stretching," is used to describe a state of wires used in leads. The term, "stretching," is being used to convey a "permanent" state of deformation wherein the wire has been deformed to fabricate gaps between adjacent coiled wires or coiling loops. In other words, after stretching, the gaps remain when the wire is in a relaxed state. Furthermore, when a lead is placed in the body, there is no stretching. The gaps remain because the lead was originally wound with the gaps or the lead was permanently deformed during fabrication by stretching or other means. The gaps, thus, remain when the wire is in a relaxed state.

Figure 22:
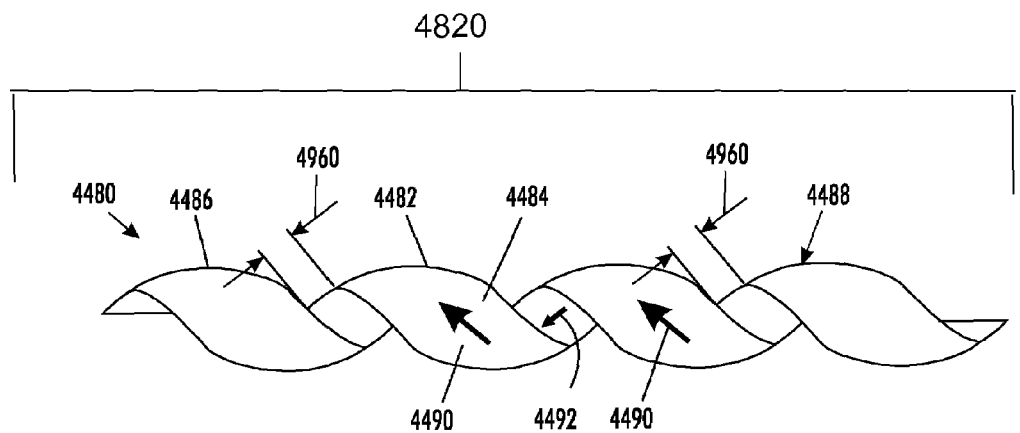
FIG. 22 illustrates another embodiment of a portion of coiled leads used in a medial device according to the concepts of the present invention.

FIG. 22 shows a portion of a coiled medical lead assembly 4480 including a region 4820 wherein the coils are stretched to form gaps or spacings 4960 between the coils in an axial direction. The coiled lead assembly 4800 is depicted in an elongated "permanent" deformed state in which adjacent coil windings are not in contact with one another due to the gaps or spacings 4960. It is to be understood that the normal non-deformed state of the lead assembly 4800 has all adjacent coiled windings in contact, as illustrated in FIG. 14.

In one embodiment of the present invention, the coiled wire 4480 may include a Teflon™ coating. The stretching, before final assembly, of the coiled wire(s) used in the final assembly of the coiled medical lead 4480 to produce the gaps or spacings 4960 forces the current 4490 and 4492 to substantially follow the curvature of the coiled winding 4820, thus forming an inductive coil. The formation of the gaps or spacings 4960 also affects the capacitance of the coiled wire medical lead 4800, thereby impacting the overall impedance of the coiled wire medical lead 4480. The gaps or spacings 4960 reduce the inter-loop capacitance without significantly reducing the loop's inductance. The inter-loop capacitance can also be reduced by interpositioning non-conductive material between the loops, the interposition non-conductive material forming the gaps or spacings 4960.

This impact upon the impedance of the coiled wire medical lead 4480, from the formation of the gaps or spacings 4960, reduces medical lead heating; such heating can be destructive to the surrounding tissue. The inductive impedance and the capacitance impedance of the coiled wire medical lead 4480 can be adjusted to minimize medical lead heating, by maximizing the overall impedance of the medical lead, by adjusting the width of the gaps or spacings 4960.

This concept can also be applied to four-conductor deep brain stimulation lead. A deep brain stimulation lead is typically four thin, insulated, coiled wires bundled within polyurethane insulation. Each wire ends in an electrode, resulting in four electrodes at the tip of the lead. Deep brain stimulation leads can be implanted bilaterally in the subthalamic nucleus or the globus pallidus interna for Parkinson's disease, or unilaterally in the left or right ventral intermediate nucleus of the thalamus. The deep brain stimulation lead delivers stimulation using either one electrode or a combination of electrodes.

In this environment, a conventional deep brain stimulation lead may consist of four, multi-fillar conductors electrically insulated from one another by a thin Teflon™ coating. The thin Teflon™ coating by itself does not sufficiently enhance the electrical impedance of the medical lead, and therefore does not provide any significant reduction in lead heating. Such a thin coating may actually increase lead capacitance, which would actually increase lead heating.

To address this problem in a deep brain stimulation lead, the present invention deforms all four wires simultaneously by stretching the lead beyond the lead's safe shear stress limit, thereby inducing permanent deformation. This stretching, before final assembly, of all four wires creates gaps or spacings between coiled wires as shown in FIG. 22 to produce gaps or spacings.

Stretching, before final assembly of the coiled wire(s) used in the final assembly of the deep brain stimulation lead to produce the gaps or spacings, forces the current to substantially follow the curvature of the coiled winding of the deep brain stimulation lead, thus forming an inductive coil. The formation of the gaps or spacings also affects the capacitance of the deep brain stimulation lead, thereby impacting the overall impedance of the deep brain stimulation lead. It is noted that the gaps or spacings can also be realized by utilizing controlled winding methods that control of the pitch of the winding of the deep brain stimulation lead to adjust and control the amount of gap or spacing between the wires.

This impact upon the impedance of the deep brain stimulation lead, from the formation of the gaps or spacings, reduces medical lead heating; such heating can be destructive to the surrounding tissue. The inductive impedance and the capacitance impedance of the deep brain stimulation lead can be adjusted to minimize medical lead heating, by maximizing the overall impedance of the medical lead, by adjusting the width of the gaps or spacings.

Figure 23:
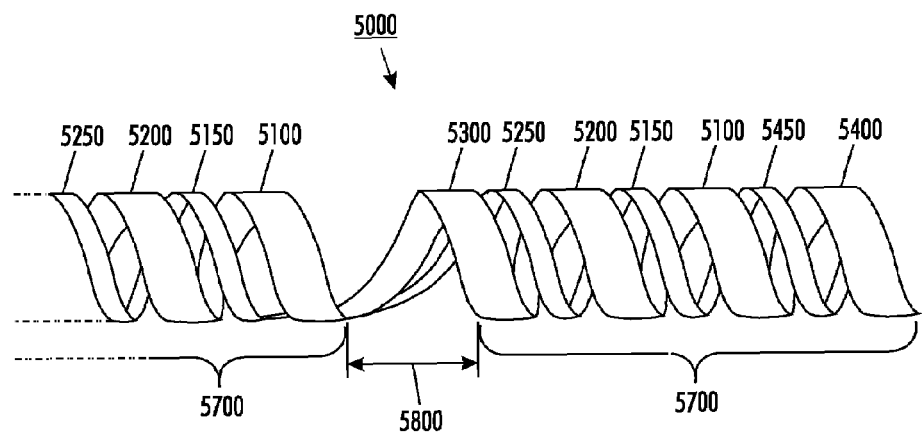
FIGS. 23 through 26 illustrate embodiments of a portion of coiled wires of a multi-wire medical lead according to the concepts of the present invention.

An example of deep brain stimulation lead using the concepts of the present invention is illustrated in FIG. 23. As illustrated in FIG. 23, the deep brain stimulation lead 5000 includes a four wire bundle represented by loops (5100, 5200, 5300, and 5400) with a ground wire represented by loops (5150, 5250, 5350, and 5450) between each of the loops (5100, 5200, 5300, and 5400). The deep brain stimulation lead 5000 is stretched to create gaps or spacings 5800 between the four wire bundle with ground wire groups 5700.

The stretching, before final assembly, of the coiled wire(s) used in the final assembly of the deep brain stimulation lead 5000 to produce the gaps or spacings 5800 forces the currents to substantially follow the curvature of the deep brain stimulation lead 5000, thus forming an inductive coil. The formation of the gaps or spacings 5800 also affects the capacitance of the deep brain stimulation lead 5000, thereby impacting the overall impedance of the deep brain stimulation lead 5000. It is noted that the gaps or spacings can also be realized by utilizing controlled winding methods that control of the pitch of the winding of the deep brain stimulation lead to adjust and control the amount of gap or spacing between the wires.

This impact upon the impedance of the deep brain stimulation lead 5000, from the formation of the gaps or spacings 5800, reduces medical lead heating; such heating can be destructive to the surrounding tissue. The inductive impedance and the capacitance impedance of the deep brain stimulation lead 5000 can be adjusted too minimize medical lead heating, by maximizing the overall impedance of the medical lead, by adjusting the width of the gaps or spacings 5800.

It is noted that the stretching can also cause gaps or spacings between the individual wires within the group to further impact the impedance of the deep brain stimulation lead 5000. The gaps or spacings 5800 reduce the inter-loop capacitance without significantly reducing the loop's inductance.

The inter-loop capacitance can also be reduced by interpositioning non-conductive material between the loops, the interposition non-conductive material forming the gaps or spacings 5800.

It is noted that the four multi-filar wires in the deep brain stimulation lead may also be of different coil diameters (i.e. being concentric) and may contain wires with different thicknesses. With respect to the concepts of the present invention, the four, concentric, "stretched conductors" will not remain in contact with one another. Hence, the stretching will increase lead impedance due to increased gap or spacing between adjacent windings within any one conductor by affecting both the capacitance and inductance of the overall lead, since conductor to conductor contact is eliminated. The increase lead impedance and decrease lead capacitance significantly reduce heating effects of the deep brain stimulation lead.

Figure 24:
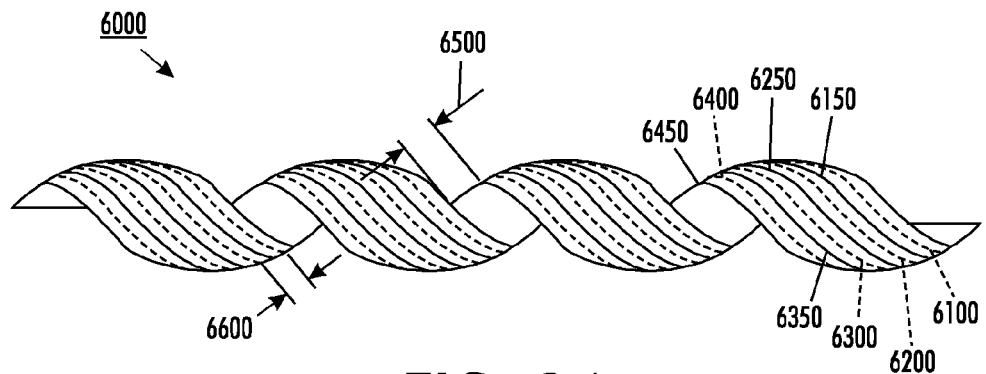

Another example of a multi-wire medical lead, such as a deep brain stimulation lead, using the concepts of the present invention is illustrated in FIG. 24. As illustrated in FIG. 24, the multi-wire medical lead 6000 includes four wires (6100, 6200, 6300, and 6400) (dotted lines). Each wire (6100, 6200, 6300, and 6400) is coated with a non-conductive sheath (6150, 6250, 6350, and 6450). The non-conductive sheath may comprise PTFE, a polymer, or a dielectric material.

The thickness of each non-conductive sheath (6150, 6250, 6350, and 6450) creates a non-conductive gap or spacing between adjacent wires (6100, 6200, 6300, and 6400). For example, the thickness of non-conductive sheaths 6150 and 6250 creates a non-conductive gap or spacing between adjacent wires 6100 and 6200.

The multi-wire medical lead 6000 can also be stretched to create gaps or spacings 6500 between the four wires (6100, 6200, 6300, and 6400). The stretching, before final assembly, of the coiled wire(s) used in the final assembly of the multi-wire medical lead 6000 to produce the gaps or spacings 6500 and the gaps or spacings formed by non-conductive sheaths (6150, 6250, 6350, and 6450) force the currents to substantially follow the curvature of the multi-wire medical lead 6000, thus forming an inductive coil. The formation of the gaps or spacings 6500 and the gaps or spacings formed by non-conductive sheaths (6150, 6250, 6350, and 6450) also affect the capacitance of the multi-wire medical lead 6000, thereby impacting the overall impedance of the multi-wire medical lead 6000. It is noted that the gaps or spacings can also be realized by utilizing controlled winding methods that control of the pitch of the winding of the multi-wire medical lead to adjust and control the amount of gap or spacing between the wires.

This impact upon the impedance of the multi-wire medical lead 6000, from the formation of the gaps or spacings 6500 and the gaps or spacings formed by non-conductive sheaths (6150, 6250, 6350, and 6450), reduces medical lead heating; such heating can be destructive to the surrounding tissue. The inductive impedance and the capacitance impedance of the multi-wire medical lead 6000 can be adjusted too minimize medical lead heating, by maximizing the overall impedance of the medical lead, by adjusting the width of the gaps or spacings 6500 and the gaps or spacings formed by non-conductive sheaths (6150, 6250, 6350, and 6450).

Figure 25:
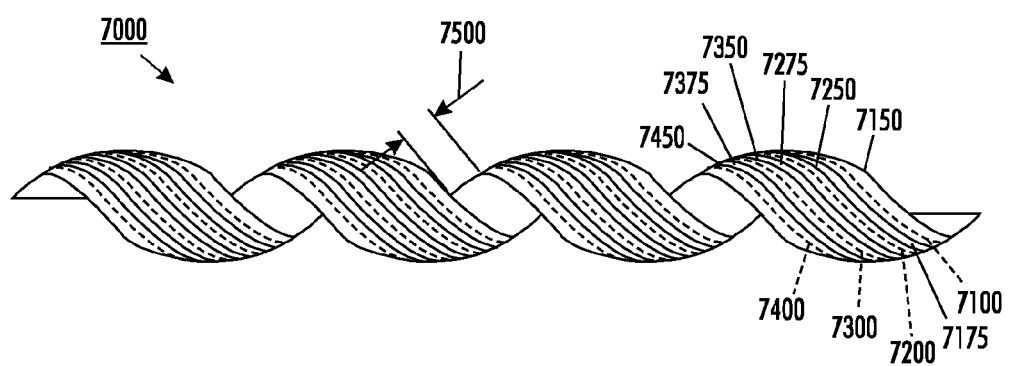

A further example of a multi-wire medical lead, such as a deep brain stimulation lead, using the concepts of the present invention is illustrated in FIG. 25. As illustrated in FIG. 25, the multi-wire medical lead 7000 includes four wires (7100, 7200, 7300, and 7400) (dotted lines). Each wire (7100, 7200, 7300, and 7400) is coated with a non-conductive sheath (7150, 7250, 7350, and 7450). The thickness of each non-conductive sheath (7150, 7250, 7350, and 7450) adds to a gap or spacing between adjacent wires (7100, 7200, 7300, and 7400). For example, the thickness of non-conductive sheaths 7150 and 7250 adds to a gap or spacing between adjacent wires 7100 and 7200.

The multi-wire medical lead 7000 can also be stretched to create gaps or spacings 7500 between the four wires (7100, 7200, 7300, and 7400). The stretching, before final assembly, of the coiled wire(s) used in the final assembly of the multi-wire medical lead 7000 can also create air gaps or spacings (7175, 7275, and 7375) between adjacent non-conductive sheath (7150, 7250, 7350, and 7450). The combination of the thickness of each non-conductive sheath (7150, 7250, 7350, and 7450) adding to a gap or spacing between adjacent wires and the air gaps or spacings (7175, 7275, and 7375) create an inter-wire gap. For example, an inter-wire gap or spacing is the combination of the thickness of non-conductive sheaths 7150 and 7250 and the air gap or spacing 7175. It is noted that the gaps or spacings can also be realized by utilizing controlled winding methods that control of the pitch of the winding of the multi-wire medical lead to adjust and control the amount of gap or spacing between the wires.

The stretching, before final assembly, of the coiled wire(s) used in the final assembly of the multi-wire medical lead 7000 to produce the gaps or spacings 7500 and the inter-wire gaps or spacings, formed by non-conductive sheaths (7150, 7250, 7350, and 7450) and the air gaps or spacings (7175, 7275, and 7375), force the currents to substantially follow the curvature of the multi-wire medical lead 7000, thus forming an inductive coil. The formation of the gaps or spacings 7500 and the inter-wire gaps or spacings, formed by non-conductive sheaths (7150, 7250, 7350, and 7450) and the air gaps or spacings (7175, 7275, and 7375), also affect the capacitance of the multi-wire medical lead 7000, thereby impacting the overall impedance of the multi-wire medical lead 7000.

This impact upon the impedance of the multi-wire medical lead 7000, from the formation of the gaps or spacings 7500 and the inter-wire gaps or spacings, formed by non-conductive sheaths (7150, 7250, 7350, and 7450) and the air gaps or spacings (7175, 7275, and 7375), reduces medical lead heating; such heating can be destructive to the surrounding tissue. The inductive impedance and the capacitance impedance of the multi-wire medical lead 7000 can be adjusted too minimize medical lead heating, by maximizing the overall impedance of the medical lead, by adjusting the width of the gaps or spacings 7500 and the inter-wire gaps or spacings, formed by non-conductive sheaths (7150, 7250, 7350, and 7450) and the air gaps or spacings (7175, 7275, and 7375).

Figure 26:
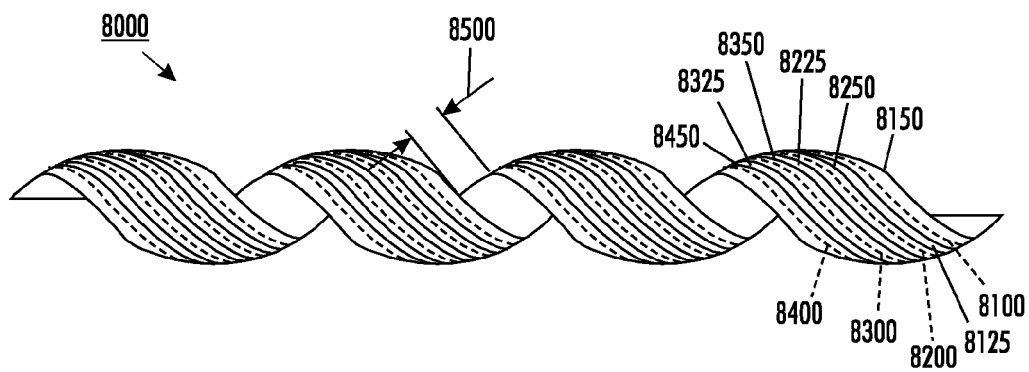

Another example of a multi-wire medical lead, such as a deep brain stimulation lead, using the concepts of the present invention is illustrated in FIG. 26. As illustrated in FIG. 26, the multi-wire medical lead 8000 includes four wires (8100, 8200, 8300, and 8400) (dotted lines). Each wire (8100, 8200, 8300, and 8400) is coated with a non-conductive sheath (8150, 8250, 8350, and 8450). The thickness of each non-conductive sheath (8150, 8250, 8350, and 8450) adds to a gap or spacing between adjacent wires (8100, 8200, 8300, and 8400). For example, the thickness of non-conductive sheaths 8150 and 8250 adds to a gap or spacing between adjacent wires 8100 and 8200.

The multi-wire medical lead 8000 is created with dummy (polymer) wires (8125, 8225, and 8325) that are formed between adjacent wires (8100, 8200, 8300, and 8400). For example, dummy (polymer) wire 8125 is formed between adjacent wires 8100 and 8200. The combination of the thickness of each PTFE sheath (8150, 8250, 8350, and 8450) adding to a gap or spacing between adjacent wires and the dummy (polymer) wires (8125, 8225, and 8325) create an inter-wire gap. For example, an inter-wire gap or spacing is the combination of the thickness of non-conductive sheaths 8150 and 8250 and the dummy (polymer) wire 8125.

The dummy (polymer) wires (8125, 8225, and 8325) of the multi-wire medical lead 8000 can also be removed to form air gaps or spacings, similar to those illustrated in FIG. 25, between adjacent non-conductive sheath (8150, 8250, 8350, and 8450). The combination of the thickness of each non-conductive sheath (8150, 8250, 8350, and 8450) adding to a gap or spacing between adjacent wires and the air gaps or spacings formed by removing the dummy (polymer) wires (8125, 8225, and 8325) create an inter-wire gap. For example, an inter-wire gap or spacing is the combination of the thickness of non-conductive sheaths 8150 and 8250 and the air gap or spacing formed by removing the dummy (polymer) wire 8125.

The multi-wire medical lead 8000 can also be stretched to create gaps or spacings 8500 between the four wires (8100, 8200, 8300, and 8400). The stretching, before final assembly, of the coiled wire(s) used in the final assembly of the multi-wire medical lead 8000 can also create air gaps or spacings (8185, 8285, and 8385) between adjacent PTFE sheath (8150, 8250, 8350, and 8450). It is noted that the gaps or spacings can also be realized by utilizing controlled winding methods that control of the pitch of the winding of the multi-wire medical lead to adjust and control the amount of gap or spacing between the wires.

The stretching, before final assembly, of the coiled wire(s) used in the final assembly of the multi-wire medical lead 8000 to produce the gaps or spacings 8500 and the inter-wire gaps or spacings force the currents to substantially follow the curvature of the multi-wire medical lead 8000, thus forming an inductive coil. The formation of the gaps or spacings 8500 and the inter-wire gaps or spacings also affect the capacitance of the multi-wire medical lead 8000, thereby impacting the overall impedance of the multi-wire medical lead 8000.

This impact upon the impedance of the multi-wire medical lead 8000, from the formation of the gaps or spacings 8500 and the inter-wire gaps or spacings reduces medical lead heating; such heating can be destructive to the surrounding tissue. The inductive impedance and the capacitance impedance of the multi-wire medical lead 8000 can be adjusted to minimize medical lead heating, by maximizing the overall impedance of the medical lead, by adjusting the width of the gaps or spacings 8500 and the inter-wire gaps or spacings.

It is noted that the various examples illustrated in FIGS. 24-26 are equally applicable to two-wire medical leads, or other medical leads having multiple wires being wound to form the coiled medical lead.

Moreover, each wire could be replaced with a very small diameter coaxial cable, and then coiled. It is noted that this embodiment introduces an additional conductor between the existing conductors. The shielding of each coaxial cable can be connected to the electronics in a signal generator canister, to the electric ground of the circuit in the signal generator canister, or other electronics.

The present invention, as set forth above, reduces the parasitic capacitance between each adjacent wire loop in the coiled lead. The parasitic capacitance makes looped wire function as an electrical short when placed in the 64 MHz radio frequency fields of a magnetic resonance scanner. The parasitic capacitance allows the current to "hop" from one loop to the other. The parasitic capacitance does not prevent high frequency signals from traveling along. By breaking up this parasitic capacitance along (between) the loops of the coiled lead, the present invention reduces the ability of the magnetic resonance scanner's induced signals from passing along the coiled lead.

It is noted that the present invention adjusts both the (parasitic) capacitance and the inductance of the lead as the windings and spacing are changed. However, the present invention only changes the capacitance when the present invention changes the dielectric material, leaving the spacing the same. So, the present invention can change both the capacitive and inductive reactance. It is also possible to achieve specific beneficial values of these parameters from these values, such as achieving resonance or preventing resonance, as well as, significantly reducing the heating of the lead.

It is noted that for a bipolar pacing lead and other multi-conductor leads, i.e. deep brain stimulation leads, pain relief leads, one or more conductors through the lead is designated to act as the ground conductor with respect to the other "signal" or "sensing" conductors making up the lead. Moreover, it is noted that a lead in a magnetic resonance imaging environment can have electromagnetic forces or voltages induced therein at every point along the lead's length and in all the conductors comprising the lead due to the rotating magnetic field formed by the magnetic resonance imaging scanner. This rotating magnetic field is often called the RF field as well as the $B_1$ field of the magnetic resonance imaging scanner.

The equation giving the induced electric field and hence the induced voltages is given be Maxwell's equation:

$$\nabla \times \vec{E} = -\frac{\partial \vec{B}}{\partial t} \tag{1}$$

For the rotating $\vec{B}_1$ field, $$\vec{B} = B_1 \sin(\omega t)\hat{x} + B_1 \cos(\omega t)\hat{y} \tag{2}$$

where $B_1$ is the magnetic amplitude function, $\omega$ is the angular frequency of the rotating magnetic field and $\hat{x}$ and $\hat{y}$ are unit vectors in the x and y axis directions, respectively.

The electric field equation is given by $$\vec{E} = -B_1 \omega (x \sin(\omega t) + y \cos(\omega t))\hat{z} \tag{3}$$

where $\hat{z}$ is the unit vector in the z-axis direction.

The induced electromagnetic force is then the line integral along the path of the lead conductors $$\text{EMF} = \int \vec{E} \circ d\vec{s} \tag{4}$$

It is noted that the amplitude function $B_1$ may be a time modulated function, e.g. a sinc($\omega t$) function, in which case the above equations are appropriately modified.

For a bipolar pacing lead, there are two conductors in the lead. Most of the time, both conductors are at the same or nearly the same electrical potential. When a pacing pulse is generated, an electrical potential difference (voltage difference) is generated between the two conductors in the lead.

Figure 27:
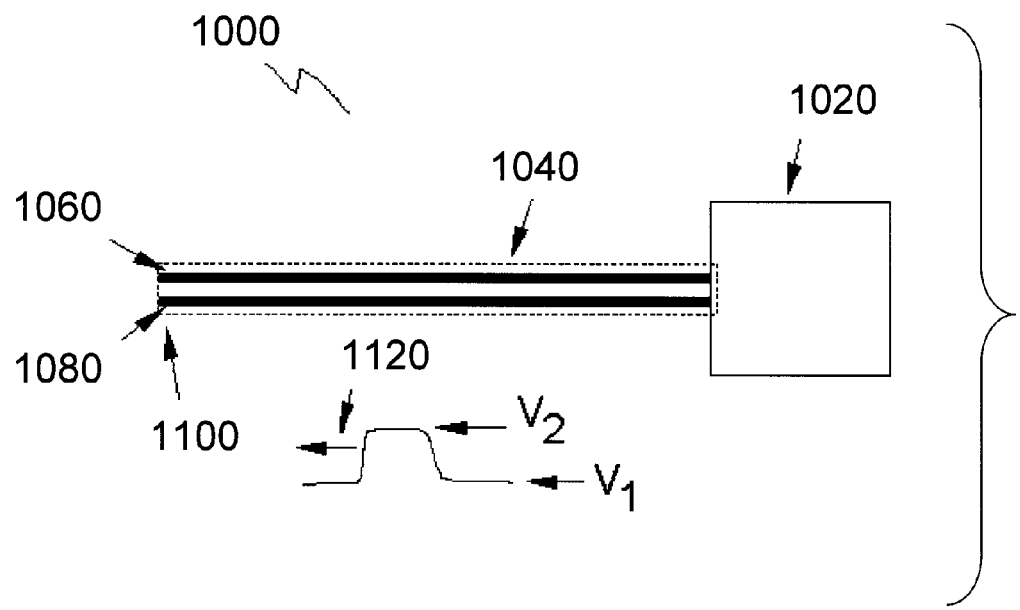
FIG. 27 illustrates a pacing system having a lead and a pulse generator according to the concepts of the present invention.

FIG. 27 depicts a pacing system 1000 having a lead 1040 and a pulse generator 1020. The lead 1040 includes two electrically isolated conductors 1060 and 1080. At the distal tip 1100, electrodes (not shown) are exposed to connect the conductors 1060 and 1080 with body tissue and/or fluids (not shown).

When a pulse is delivered 1120 from the generator 1020, a voltage difference between the two conductors 1060 and 1080 is developed. More specifically, as illustrated in FIG. 27, when a pulse 1120 is generated on conductor 1060, the voltage on that conductor 1060 rises to $V_2$ for the duration of the pulse, pulsewidth, while the voltage on conductor 1080 is maintained at voltage $V_1$. This creates a temporary voltage difference, $|V_2-V_1|$ between the two conductors 1060 and 1080.

Figure 28:
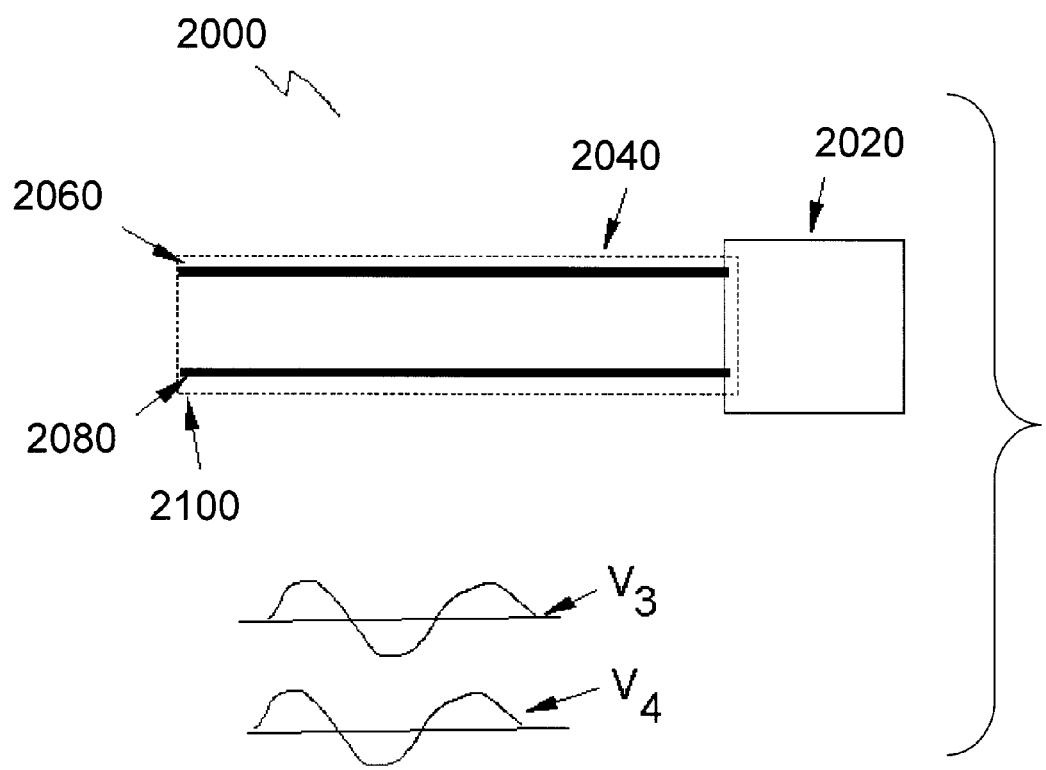
FIG. 28 illustrates a bipolar pacing system in magnetic resonance imaging scanner environment according to the concepts of the present invention.

On the other hand, when the two conductors 1060 and 1080 are in a magnetic resonance imaging scanner environment, the B1 field produced by the magnetic resonance imaging scanner induces voltages in the two conductors 1060 and 1080 of the lead 1040. The induced voltages are essentially equal in magnitude. FIG. 28 provides an illustration of this situation.

FIG. 28 illustrates a bipolar pacing system 2000 in magnetic resonance imaging scanner environment. As illustrated, a magnetic resonance imaging scanner induces voltages $V_3$ and $V_4$ in two conductors 2060 and 2080. As noted above, these induced voltages are essentially equal in magnitude.

If it is assumed that conductor 2060 is the "ground" conductor and conductor 2080 is the "signal conductor, the "ground" conductor's potential is essentially the equal to the "signal" conductor's potential. Therefore, there is no effective "ground" at the distal tip of the pacing lead 2100 in which to implement a voltage filtering mechanism.

In order for various filters (e.g., a low pass filter) to perform correctly, a significant potential difference must exist. More specifically, when a filter is introduced into the distal tip of a lead to filter or block induced voltages due to the magnetic resonance imaging scanner's radio-frequency field, a significant potential difference must exist between the conductors 2060 and 2080 for the filter to operate properly. FIG. 29 provides an illustration of this situation.

FIG. 29 illustrates a pacing system 2000 with a lead 2040 including two conductors 2060 and 2080 with a low pass filter being implemented by the insertion of a capacitor 2180 between the two conductors 2060 and 2080. Since the voltages in the two conductors 2060 and 2080 induced by the magnetic resonance imaging scanner's B1 field are essentially equal in magnitude, charge does not buildup on each side (2200 and 2220) of the capacitor 2180. Therefore, the low pass filter (capacitor 2180) fails to filter the voltages induced by the magnetic resonance imaging scanner's B1 field.

It is noted that some minor potential difference may occur between the two conductors due to the different construction of the lead. For example, one conductor may be a wound conductor having a different radius than the other conductor. However such a potential difference is not usually sufficient for the filter to function adequately. To ensure an effective potential difference a voltage compensation device is utilized with the lead. An example of a voltage compensation device utilized with a lead is illustrated in FIG. 30.

FIG. 30 illustrates a pacing system comprising a lead 3040, a pulse generator 3020, and a voltage compensation component 3300. The voltage compensation component 3300 provides a compensation voltage on conductor 3060 so that there is a sufficient voltage difference at the distal tip 3100. This compensation voltage enable the filter (capacitor 3180) to effectively function in blocking the induced current in the conductor 3080 from passing through the distal tip electrode of the conductor 3080 and into the body tissue and/or fluid.

It is noted that the voltage compensation component 3300 may be constructed so as to be completely outside the pulse generator 3020, may be positioned completely inside the pulse generator 302, or may be partially inside and partially outside the pulse generator 3020.

Figure 31:
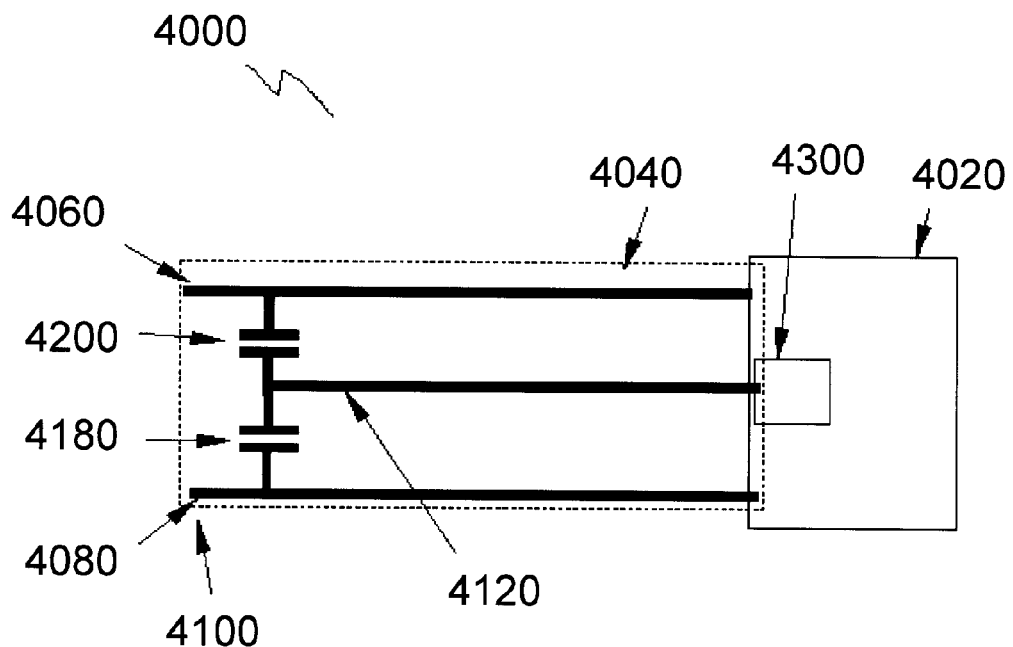
FIG. 31 illustrates another implementation of a voltage compensation device utilized with a lead in which an additional conductor is inserted into the lead together with the two conductors according to the concepts of the present invention.

FIG. 31 depicts another implementation of a voltage compensation device utilized with a lead in which an additional conductor 4120 is inserted into the lead 4040 together with the two conductors 4060 and 4080. In this embodiment, the voltage compensation component 4300 is electrically connected to the conductor 4120. The voltage compensation component 4300 generates a compensation voltage when there are voltages in the three conductors induced by the magnetic resonance imaging scanner's B1 field. This compensation voltage provides a sufficient voltage difference between the conductor 4120 and the conductors 4060 and 4080 so that filters 4200 and 4180 placed in the distal tip 4100 can effectively block the voltages and currents from passing from the conductors 4060 and 4080, through electrodes (not shown), and into the body tissue and/or fluids.

In one embodiment, the voltage compensation unit 4300 may be a wound wire having N windings or turns. The windings or turns are oriented and positioned to form a coil such that when the magnetic resonance imaging scanner's B1 field is applied to the patient's body, the induced EMF along the lead's conductor, as explained in equations (1) through (4) above, is canceled by the EMF induced in the coil due to Lenz's Law, which states that for a coil with N turns $$EMF = -N\frac{d\varphi}{dt} \tag{5}$$

where $\varphi$ is the magnetic flux $$\varphi = \vec{B} \circ \vec{A} \tag{6}$$

where $\vec{B}$ is the magnetic induction field (B1 field) and $\vec{A}$ is the coil's perpendicular area vector.

In another embodiment, the voltage compensation unit 4300 is connected to a power source in the pulse generator. The voltage compensation unit 4300 generates a desired compensating voltage. Moreover, the voltage compensation unit 4300 may include a sensor or sensors to determine when a compensating voltage is required.

Such sensors may be a magnetic field sensor that senses the presence of the magnetic resonance imaging scanner's B1 field. In this embodiment, if a sensor detects the presence of the magnetic resonance imaging scanner's B1 field, the voltage compensation unit 4300 generates the appropriate compensating voltage.

The sensor may also sense the voltage on a conductor within the lead so as to determine when a voltage is being induced or a voltage level is out of range a predetermined operating range. The information from the sensor can be used to trigger the application of an appropriate compensating voltage, as well as, the magnitude and/or frequency of the appropriate compensating voltage.

Furthermore, the sensors may also sense the voltages on all of the conductors within the lead so as to determine when a voltage is being induced on a particular conductor or a voltage level is out of range a predetermined operating range. The information from the sensors can be used to trigger the application of an appropriate compensating voltage to the appropriate conductor, as well as, the magnitude and/or frequency of the appropriate compensating voltage for the appropriate conductor.

Figure 32:
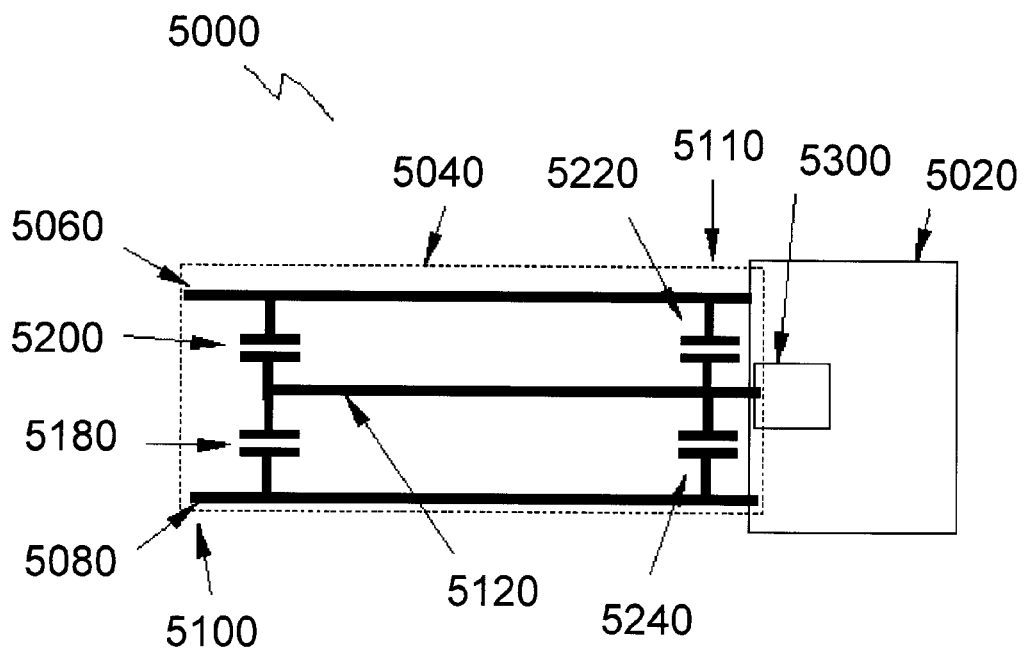
FIG. 32 illustrates another implementation of a voltage compensation device according to the concepts of the present invention.

In a further embodiment, as illustrated in FIG. 32, filters 5180, 5200, 5220, and 5240 are placed at both the distal end 5100 and the proximal end 5110 of lead 5040. The filters 5180 and 5200 at the distal end 5100 of the lead 5040 prevent harmful magnetic resonance imaging induced voltages and currents from passing through the lead's distal tip electrodes (not shown). On the other hand, filters 5220 and 5240 at the proximal end 5110 of the lead 5040 prevent harmful magnetic resonance imaging induced voltages and currents from passing into the pulse generator's circuitry (not shown) contained within pulse generator 5020.

In this embodiment, the voltage compensation component 5300 is electrically connected to the conductor 5120. The voltage compensation component 5300 generates a compensation voltage when there are voltages in the three conductors induced by the magnetic resonance imaging scanner's B1 field. This compensation voltage provides a sufficient voltage difference between the conductor 5120 and the conductors 5060 and 5080 so that filters 5200 and 5180 placed in the distal tip 5100 can effectively block the voltages and currents from passing from the conductors 5060 and 5080, through electrodes (not shown), and into the body tissue and/or fluids. The compensation voltage provides a sufficient voltage difference between the conductor 5120 and the conductors 5060 and 5080 so that filters 5220 and 5240 placed in the proximal tip 5110 can effectively block the voltages and currents from passing from the conductors 5060 and 5080 into the pulse generator's circuitry (not shown) contained within pulse generator 5020.

In one embodiment, the voltage compensation unit 5300 may be a wound wire having N windings or turns. The windings or turns are oriented and positioned to form a coil such that when the magnetic resonance imaging scanner's B1 field is applied to the patient's body, the induced EMF along the lead's conductor, as explained in equations (1) through (4) above, is canceled by the EMF induced in the coil due to Lenz's Law, which states that for a coil with N turns $$EMF = -N\frac{d\varphi}{dt} \quad (5)$$

where $\varphi$ is the magnetic flux $$\varphi = \vec{B} \circ \vec{A} \quad (6)$$

where $\vec{B}$ is the magnetic induction field (B1 field) and $\vec{A}$ is the coil's perpendicular area vector.

In another embodiment, the voltage compensation unit 5300 is connected to a power source in the pulse generator. The voltage compensation unit 5300 generates a desired compensating voltage. Moreover, the voltage compensation unit 5300 may include a sensor or sensors to determine when a compensating voltage is required.

Such sensors may be a magnetic field sensor that senses the presence of the magnetic resonance imaging scanner's B1 field. In this embodiment, if a sensor detects the presence of the magnetic resonance imaging scanner's B1 field, the voltage compensation unit 5300 generates the appropriate compensating voltage.

The sensor may also sense the voltage on a conductor within the lead so as to determine when a voltage is being induced or a voltage level is out of range a predetermined operating range. The information from the sensor can be used to trigger the application of an appropriate compensating voltage, as well as, the magnitude and/or frequency of the appropriate compensating voltage.

Furthermore, the sensors may also sense the voltages on all of the conductors within the lead so as to determine when a voltage is being induced on a particular conductor or a voltage level is out of range a predetermined operating range. The information from the sensors can be used to trigger the application of an appropriate compensating voltage to the appropriate conductor, as well as, the magnitude and/or frequency of the appropriate compensating voltage for the appropriate conductor.

In summary, a system reduces the effects of magnetic resonance imaging induced signals to a safe level having a medical device that includes a housing having electronic circuitry therein, a first lead to provide an electrical path for a stimulation signal generated by the electronic circuitry to be applied to a desired tissue region, a second lead to provide an electrical path for a sensed physiological condition of the desired tissue region to be communicated to the electronic circuitry, and a third lead to provide an electrical ground. A diode is connected to the first lead to significantly reduce magnetic resonance imaging induced signals from traveling along the first lead to the electronic circuitry.

In the various embodiments described above, the filter may be an inductor, a resistor, and/or a capacitor. Moreover, in the various embodiments described above, the voltage compensation unit may be a source that generates an electrical potential opposite to that which would be induced by the magnetic resonance imaging switched gradient fields so as to reduce voltages induced by the magnetic resonance imaging switched gradient fields to a safe level or a coil that generates a magnetic resonance imaging switched gradient field induced current opposite to that which would be induced by the magnetic resonance imaging switched gradient fields in the leads so as to reduce voltages induced by the magnetic resonance imaging switched gradient fields to a safe level wherein the coil may be curved in three different spatial directions. The voltage compensation unit having the coil may also include an orientation subsystem for changing a spatial orientation of the coil to modify the strength of the magnetic resonance imaging switched gradient field induced current.

The voltage compensation unit may include a plurality of coils, each coil generating a magnetic resonance imaging switched gradient field induced current opposite to that which would be induced by the magnetic resonance imaging switched gradient fields in the leads so as to reduce voltages induced by the magnetic resonance imaging switched gradient fields to a safe level, and a switch connecting independently a number of the plurality of the coils, the number of connected coils corresponding to an amount of the voltage induced by the magnetic resonance imaging switched gradient fields and a current level produced in each coil when the sensor senses the application of switched magnetic resonance imaging gradient fields wherein the coils are curved in three different spatial directions. The voltage compensation unit may also include an orientation subsystem for changing a spatial orientation of the coils to modify the strength of the magnetic resonance imaging switched gradient field induced currents.

The voltage compensation unit may be three orthogonally planar coils, each coil generating a magnetic resonance imaging switched gradient field induced current opposite to that which would be induced by the magnetic resonance imaging switched gradient fields in the leads so as to reduce voltages induced by the magnetic resonance imaging switched gradient fields to a safe level, and a switch connecting independently a number of the coils, the number of connected coils corresponding to an amount of the voltage induced by the magnetic resonance imaging switched gradient fields and a current level produced in each coil when the sensor senses the application of switched magnetic resonance imaging gradient fields. The voltage compensation unit may also include an orientation subsystem for changing a spatial orientation of the coils to modify the strength of the magnetic resonance imaging switched gradient field induced currents wherein each coil defines a distinct plane that transverses the magnetic resonance imaging switched gradient fields.

The voltage compensation unit may also include a receiver to receive a signal from a magnetic resonance imaging system indicating an application of switched magnetic resonance imaging gradient fields. The voltage compensation unit may be a source that generates an electrical potential opposite to that which would be induced by the magnetic resonance imaging switched gradient fields so as to reduce voltages induced by the magnetic resonance imaging switched gradient fields to a safe level or a coil that generates a magnetic resonance imaging switched gradient field induced current opposite to that which would be induced by the magnetic resonance imaging switched gradient fields in the leads so as to reduce voltages induced by the magnetic resonance imaging switched gradient fields to a safe level wherein the coil may be curved in three different spatial directions. The voltage compensation unit having the coil may also include an orientation subsystem for changing a spatial orientation of the coil to modify the strength of the magnetic resonance imaging switched gradient field induced current.

The voltage compensation unit may include a plurality of coils, each coil generating a magnetic resonance imaging switched gradient field induced current opposite to that which would be induced by the magnetic resonance imaging switched gradient fields in the leads so as to reduce voltages induced by the magnetic resonance imaging switched gradient fields to a safe level, and a switch connecting independently a number of the plurality of the coils, the number of connected coils corresponding to an amount of the voltage induced by the magnetic resonance imaging switched gradient fields and a current level produced in each coil when the sensor senses the application of switched magnetic resonance imaging gradient fields wherein the coils are curved in three different spatial directions. The voltage compensation unit may also include an orientation subsystem for changing a spatial orientation of the coils to modify the strength of the magnetic resonance imaging switched gradient field induced currents.

The voltage compensation unit may be three orthogonally planar coils, each coil generating a magnetic resonance imaging switched gradient field induced current opposite to that which would be induced by the magnetic resonance imaging switched gradient fields in the leads so as to reduce voltages induced by the magnetic resonance imaging switched gradient fields to a safe level, and a switch connecting independently a number of the coils, the number of connected coils corresponding to an amount of the voltage induced by the magnetic resonance imaging switched gradient fields and a current level produced in each coil when the sensor senses the application of switched magnetic resonance imaging gradient fields. The voltage compensation unit may also include an orientation subsystem for changing a spatial orientation of the coils to modify the strength of the magnetic resonance imaging switched gradient field induced currents wherein each coil defines a distinct plane that transverses the magnetic resonance imaging switched gradient fields.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a coil, a voltage compensation unit, that generates a magnetic resonance imaging switched gradient field induced current opposite to that which would be induced by the magnetic resonance imaging switched gradient fields in the medical device electrical lead so as to reduce voltages induced by the magnetic resonance imaging switched gradient fields to a safe level. The coil may be curved in three different spatial directions.

The embodiment may further include an orientation subsystem for changing a spatial orientation of the coil to modify the strength of the magnetic resonance imaging switched gradient field induced current.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a plurality of coils, a voltage compensation unit, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device electrical lead so as to reduce voltages induced by the magnetic resonance imaging switched gradient fields to a safe level. The coil may be curved in three different spatial directions.

The embodiment may further include an orientation subsystem for changing a spatial orientation of the coil to modify the strength of the magnetic resonance imaging switched gradient field induced current.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and three orthogonally planar coils, a voltage compensation unit, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device electrical lead so as to reduce voltages induced by the magnetic resonance imaging switched gradient fields to a safe level.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a voltage compensation unit. The voltage compensation unit includes a plurality of coils, each coil generating a magnetic resonance imaging switched gradient field induced current; a sensor to measure a strength of voltages induced by the magnetic resonance imaging switched gradient fields; and a switching device, operatively connected to the sensor and plurality of coils, to operatively connect a number of the plurality of coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a voltage compensation unit. The voltage compensation unit includes three orthogonally planar coils, each coil generating a magnetic resonance imaging switched gradient field induced current; a sensor to measure a strength of voltages induced by the magnetic resonance imaging switched gradient fields; and a switching device, operatively connected to the sensor and the coils, to operatively connect a number of the coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a voltage compensation unit. The voltage compensation unit includes a plurality of coils, each coil generating a magnetic resonance imaging switched gradient field induced current; a transceiver to receive a signal indicating a number of coils to be connected; and a switching device, operatively connected to the transceiver and plurality of coils, to operatively connect a number of the plurality of coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to an electrical lead component for a medical device that reduces the effects of magnetic resonance imaging induced signals to a safe level. The electrical lead component includes a medical device electrical lead capable of providing an electrical path to a desired tissue region and a voltage compensation unit. The voltage compensation unit includes three orthogonally planar coils, each coil generating a magnetic resonance imaging switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level.

In a further embodiment, the present invention is directed to a medical device that reduces the effects of magnetic resonance imaging induced signals to a safe level. The medical device includes a medical device capable of providing medical treatment to a desired tissue region and a coil, a voltage compensation unit, that generates a magnetic resonance imaging switched gradient field induced current opposite to that which would be induced by the magnetic resonance imaging switched gradient fields in the medical device so as to reduce voltages induced by the magnetic resonance imaging switched gradient fields to a safe level. The coil may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a medical device that reduces the effects of magnetic resonance imaging induced signals to a safe level. The medical device includes a medical device capable of providing medical treatment to a desired tissue region and a plurality of coils, a voltage compensation unit, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a medical device that reduces the effects of magnetic resonance imaging induced signals to a safe level. The medical device includes a medical device capable of providing medical treatment to a desired tissue region and three orthogonally planar coils, a voltage compensation unit, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device so as to reduce voltages induced by the magnetic resonance imaging switched gradient fields to a safe level.

In a further embodiment, the present invention is directed to a medical device that reduces the effects of magnetic resonance imaging induced signals to a safe level. The medical device includes a medical device capable of providing medical treatment to a desired tissue region and a voltage compensation unit. The voltage compensation unit includes a plurality of coils, each coil generating a magnetic resonance imaging switched gradient field induced current; a sensor to measure a strength of voltages induced by the magnetic resonance imaging switched gradient fields; and a switching device, operatively connected to the sensor and plurality of coils, to operatively connect a number of the plurality of coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a medical device that reduces the effects of magnetic resonance imaging induced signals to a safe level. The medical device includes a medical device capable of providing medical treatment to a desired tissue region and a voltage compensation unit. The voltage compensation unit includes three orthogonally planar coil, each coil generating a magnetic resonance imaging switched gradient field induced current; a sensor to measure a strength of voltages induced by the magnetic resonance imaging switched gradient fields; and a switching device, operatively connected to the sensor and plurality of coils, to operatively connect a number of the plurality of coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device so as to reduce voltages induced by the magnetic resonance imaging switched gradient fields to a safe level.

In a further embodiment, the present invention is directed to a medical device that reduces the effects of magnetic resonance imaging induced signals to a safe level. The medical device includes a medical device capable of providing medical treatment to a desired tissue region and a voltage compensation unit. The voltage compensation unit includes a plurality of coils, each coil generating a magnetic resonance imaging switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a medical device that reduces the effects of magnetic resonance imaging induced signals to a safe level. The medical device includes a medical device capable of providing medical treatment to a desired tissue region and a voltage compensation unit. The voltage compensation unit includes three orthogonally planar coil, each coil generating a magnetic resonance imaging switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level.

In a further embodiment, the present invention is directed to a voltage control unit that reduces the effects of magnetic resonance imaging induced signals upon a medical device to a safe level. The voltage control unit includes a coil that generates a magnetic resonance imaging switched gradient field induced current opposite to that which would be induced by the magnetic resonance imaging switched gradient fields in the medical device so as to reduce voltages induced by the magnetic resonance imaging switched gradient fields to a safe level. The coil may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a voltage control unit that reduces the effects of magnetic resonance imaging induced signals upon a medical device to a safe level. The voltage control unit includes a plurality of coils, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a voltage control unit that reduces the effects of magnetic resonance imaging induced signals upon a medical device to a safe level. The voltage control unit includes three orthogonally planar coils, each coil generating a magnetic resonance imaging switched gradient field induced current such a combination of the magnetic resonance imaging switched gradient field induced currents provide a combined current that is opposite to that which would be induced by the magnetic resonance imaging switched gradient fields in the medical device so as to reduce voltages induced by the magnetic resonance imaging switched gradient fields to a safe level.

In a further embodiment, the present invention is directed to a voltage control unit that reduces the effects of magnetic resonance imaging induced signals upon a medical device to a safe level. The voltage control unit includes a plurality of coils, each coil generating a magnetic resonance imaging switched gradient field induced current; a sensor to measure a strength of voltages induced by the magnetic resonance imaging switched gradient fields; and a switching device, operatively connected to the sensor and plurality of coils, to operatively connect a number of the plurality of coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a voltage control unit that reduces the effects of magnetic resonance imaging induced signals upon a medical device to a safe level. The voltage control unit includes three orthogonally planar coil, each coil generating a magnetic resonance imaging switched gradient field induced current; a sensor to measure a strength of voltages induced by the magnetic resonance imaging switched gradient fields; and a switching device, operatively connected to the sensor and plurality of coils, to operatively connect a number of the plurality of coils in response to the measured strength of voltages induced by the magnetic resonance imaging switched gradient fields such that a combination of the magnetic resonance imaging switched gradient field induced currents produced by the number of operatively connected coils provide a combined current that is opposite to that which would be induced by the magnetic resonance imaging switched gradient fields in the medical device so as to reduce voltages induced by the magnetic resonance imaging switched gradient fields to a safe level.

In a further embodiment, the present invention is directed to a voltage control unit that reduces the effects of magnetic resonance imaging induced signals upon a medical device to a safe level. The voltage control unit includes a plurality of coils, each coil generating a magnetic resonance imaging switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level. The coils may be curved in three different spatial directions.

The embodiment may further include an orientation subsystem for changing a spatial orientation of the coil to modify the strength of the magnetic resonance imaging switched gradient field induced current.

In a further embodiment, the present invention is directed to a voltage control unit that reduces the effects of magnetic resonance imaging induced signals upon a medical device to a safe level. The voltage control unit includes three orthogonally planar coil, each coil generating a magnetic resonance imaging switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the magnetic resonance imaging switched gradient field induced currents produced by the number of operatively connected coils provide a combined current that is opposite to that which would be induced by the magnetic resonance imaging switched gradient fields in the medical device electrical lead so as to reduce voltages induced by the magnetic resonance imaging switched gradient fields to a safe level.

In a further embodiment, the present invention is directed to a lead for medical applications that reduces the effects of magnetic resonance imaging induced signals to a safe level. The lead includes two coiled conductive strands forming a spring-like configuration such that current flows over a surface thereof, through contact points between adjacent loops of the coiled conductive strands, and an insulating coating formed over a portion of the two coiled conductive strands such that an inline inductive element is formed, the current flowing along a curvature of the two coiled conductive strands in the insulating coated portion of two coiled conductive strands.

This embodiment may further include a ferrite material positioned in the portion of the two-coiled conductive strands having the insulating coating formed thereon.

In a further embodiment, the present invention is directed to a lead for medical applications that reduces the effects of magnetic resonance imaging induced signals to a safe level. The lead includes two coiled conductive strands forming a spring-like configuration such that current flows over a surface thereof, through contact points between adjacent loops of the coiled conductive strands, and an adjustable resistive material formed over a portion of the two coiled conductive strands such that an inline inductive element is formed, the current flowing along a curvature of the two coiled conductive strands in the adjustable resistive material portion of two coiled conductive strands, an inductance of the inline inductive element being adjusted by adjusting the resistive properties of the adjustable resistive material.

This embodiment may further include a ferrite material positioned in the portion of the two-coiled conductive strands having the insulating coating formed thereon.

In a further embodiment, the present invention is directed to a voltage compensation unit for reducing the effects of induced voltages upon a medical device to a safe level. The voltage compensation unit includes a connection device to provide an electrical connection to the medical device; a sensing circuit to voltages of conductive components in the medical device; and a compensation circuit, operatively connected to the sensing circuit and responsive thereto, to provide opposing voltages to the medical device to reduce the effects of induced voltages caused by changing magnetic fields.

This embodiment may also include a power supply, such as a battery or a connection to an external power source. The embodiment may include a second sensing circuit to detect the changing magnetic fields and a compensation circuit, connected to the second sensing circuit and responsive thereto, to synchronize application of the opposing voltages to the medical device with the sensed changing magnetic fields.

In a further embodiment, the present invention is directed to a voltage compensation unit for reducing the effects of induced voltages upon a medical device to a safe level. The voltage compensation unit includes a connection device to provide an electrical connection to the medical device; a sensing circuit to detect changing magnetic fields; and a compensation circuit, operatively connected to the sensing circuit and responsive thereto, to synchronize application of opposing voltages to the medical device with the sensed changing magnetic fields, the opposing voltages reducing the effects of induced voltages caused by the changing magnetic fields.

This embodiment may also include a power supply, such as a battery or a connection to an external power source.

In a further embodiment, the present invention is directed to a voltage compensation unit for reducing the effects of induced voltages upon a medical device to a safe level. The voltage compensation unit includes a connection device to provide an electrical connection to the medical device; a communication circuit, communicatively linked to a magnetic resonance imaging system, to receive information associated with a start and end of an application of changing magnetic fields produced by the magnetic resonance imaging system; and a compensation circuit, operatively connected to the communication circuit and responsive thereto, to synchronize application of opposing voltages to the medical device with the sensed changing magnetic fields, the opposing voltages reducing the effects of induced voltages caused by the changing magnetic fields.

This embodiment may also include a power supply, such as a battery or a connection to an external power source. The communication circuit may receive information associated with field strengths to be applied by the magnetic resonance imaging system, and the compensation circuit would apply opposing voltages in accordance with communicated applied field strengths. The communication circuit may receive the information through electrical wires, coaxial wires, shielded wires, optical fibers, and/or a radio-frequency transmitter/receiver.

In a further embodiment, the present invention is directed to a voltage compensation unit for reducing the effects of induced voltages upon a medical device to a safe level. The voltage compensation unit includes a connection device to provide an electrical connection to the medical device; a communication circuit, communicatively linked to a magnetic resonance imaging system, to receive information associated with a start and end of an application of changing magnetic fields produced by the magnetic resonance imaging system; and a compensation circuit, operatively connected to the communication circuit and responsive thereto, to apply opposing voltages to the medical device, the opposing voltages reducing the effects of induced voltages caused by the changing magnetic fields.

This embodiment may also include a power supply, such as a battery or a connection to an external power source. The communication circuit may receive information associated with field strengths to be applied by the magnetic resonance imaging system, and the compensation circuit would apply opposing voltages in accordance with communicated applied field strengths. The communication circuit may receive the information through electrical wires, coaxial wires, shielded wires, optical fibers, and/or a radio-frequency transmitter/receiver.

In a further embodiment, the present invention is directed to a medical assembly. The medical assembly includes a multi-wire lead having a plurality of loops. The multi-wire lead has a gap region and a non-gap region. The gap region has adjacent loops of the multi-wire lead with gaps therebetween so as to form impedance in the multi-wire lead. The non-gap region has adjacent loops of the multi-wire lead with no gaps therebetween. The gaps may provide inter-loop capacitance. The multi-wire lead may have a plurality of gap regions, each gap region having a non-gap region therebetween.

In another embodiment, the present invention is directed to a medical assembly. The medical assembly includes a multi-wire lead having a plurality of wires, each wire having a plurality of loops. The multi-wire lead has a gap region and a non-gap region, the gap region having a first gap between a loop of a first wire and a loop of a second wire and the non-gap region having a second gap between a loop of a first wire and a loop of a second wire. The first gap is greater than said second gap. The gap region may form impedance in the multi-wire lead.

In another embodiment, the present invention is directed to a medical assembly. The medical assembly includes a multi-wire lead having a plurality of wires, each wire having a plurality of loops. The multi-wire lead has a gap region and a non-gap region, the gap region having a first lead intra-loop gap between a first loop of a first wire and a second loop of the first wire and the non-gap region having a second lead intra-loop gap between a third loop of the first wire and a fourth loop of the first wire. The first lead intra-loop gap is greater than said lead intra-loop second gap. The gap region may form impedance in the multi-wire lead. The multi-wire lead may have an intra-loop inter-wire gap between adjacent wires.

In another embodiment, the present invention is directed to a medical assembly. The medical assembly includes a multi-wire lead having a plurality of conductive wires and a plurality of non-conductive wires, each conductive wire having a plurality of loops, each non-conductive wire having a plurality of loops. The loops of a non-conductive wire are positioned between adjacent loops of two conductive wires to form a lead intra-loop non-conductive gap between the adjacent loops of two conductive wires. The multi-wire lead may have a gap region and a non-gap region, the gap region having a first lead intra-loop gap between a first loop of a first wire and a second loop of the first wire and the non-gap region having a second lead intra-loop gap between a third loop of the first wire and a fourth loop of the first wire. The first lead intra-loop gap is greater than said lead intra-loop second gap. The gap region may form different impedance in the gap region than an impedance in the non-gap region.

The equation giving the induced Electric Field dues to a rotation magnetic field, as in a magnetic resonance imaging scanner is given be Maxwell's equation:

$$\nabla \times \vec{E} = -\frac{\partial \vec{B}}{\partial t} \quad (1)$$

For the rotating $\vec{B}_1$ field, $$\vec{B} = B_1 \sin(\omega t)\hat{x} + B_1 \cos(\omega t)\hat{y} \quad (2)$$

where $B_1$ is the magnetic amplitude function, $\omega$ is the angular frequency of the rotating magnetic field and $\hat{x}$ and $\hat{y}$ are unit vectors in the x and y axis directions, respectively, the electric field equation is given by $$\vec{E} = -B_1 \omega (x \sin(\omega t) + y \cos(\omega t))\hat{z} \quad (3)$$

where $\hat{z}$ is the unit vector in the z-axis direction.

The induced EMF is then the line integral along the path of the lead conductors $$\text{EMF} = \int \vec{E} \circ d\vec{s} \quad (4)$$

The induced EMF in a coil of wire is as given by Lenz's Law, which states that for a coil with N-turns $$EMF = -N \frac{d\varphi}{dt} \quad (5)$$

where φ is the magnetic flux $$\varphi = \vec{B} \circ \vec{A} \quad (6)$$

where $\vec{B}$ is the magnetic induction field ($B_1$ field) and $\vec{A}$ is the coil's perpendicular area vector.

A lead comprising conductive wire may be so constructed that when placed in a rotating magnetic field, with appropriate orientation, that the induced EMF generated through the mechanism outline in equations (1) through (4) along a short section of the conductive wire may be essentially canceled by the induced EMF generated through the mechanism outlined in equations (5) and (6) applied to an adjacent short section of the conductive wire.

Figure 33:
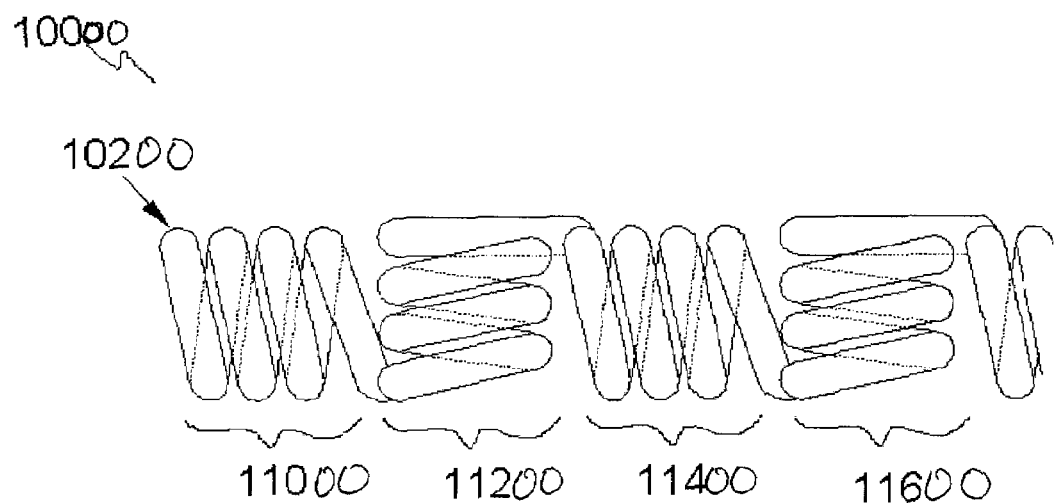
FIG. 33 illustrates a coiled conductive wire according to the concepts of the present invention.

Such a coiled conductive wire is illustrated in FIG. 33. The coiled wire 10200 comprises short sections 11000, 11400 coiled along the axis of the lead length and short sections 11200, 11600 coiled perpendicular to the leads length.

Figure 34:
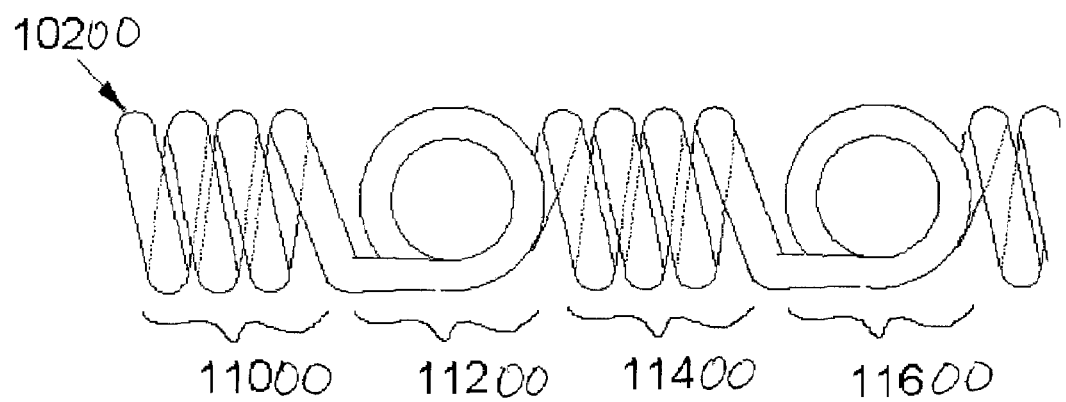
FIG. 34 illustrates a coiled conductive wire according to the concepts of the present invention.

FIG. 34 depicts the same coiled wire section as in FIG. 33 from a different orientation.

Different coiling designs may be needed for leads placed in different paths through the body. Because each different path will have a different amount of the lead running parallel to the magnetic resonance imaging scanner's z-axis, a different number of perpendicular coils 11200, 11600 per unit length will be needed to eliminate the magnetic resonance imaging induced current through the lead.

In another embodiment, the number of perpendicular coils 11200, 11600 per unit length of the lead is varied along the leads total length such that when positioned in the patient's body, those sections of the lead which run essentially perpendicular to the scanner's z-axis (in an xy-plane) has little to no perpendicular coils 11200, 11600 while those sections of the lead which run essentially parallel to the scanner's z-axis have many perpendicular coils 11200, 11600.

It is important that the lead be oriented properly. Improperly orienting the coiled lead (for example, rotating the lead about its length axis by 180 degrees) will enhance the magnetic resonance imaging induced currents, not retard them.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. A medical apparatus, comprising:
   a medical assist device to process signals to relating biological functions;
   a first lead operatively connected to said medical assist device, said first lead having a distal end and a proximal end;
   a second lead operatively connected to said medical assist device, said second lead having a distal end and a proximal end;
   a first electrode operatively connected to said distal end of said first lead;
   a second electrode operatively connected to said distal end of said second lead;
   a filter circuit operatively connected near said distal end of said first lead and said distal end of said second lead; and
   a compensation circuit, operatively connected to said first lead, to provide a compensation voltage to enable said filter to effectively block changing magnetic fields induced current in said second lead from passing through said second electrode of said distal end of said second lead.

2. The medical apparatus as claimed in claim 1, wherein said compensation circuit comprises:
   a sensing circuit to sense voltages induced in said first lead, the voltages being induced by changing magnetic fields; and
   a voltage compensation circuit, operatively connected to said sensing circuit and responsive thereto, to provide said compensation voltage.

3. The medical apparatus as claimed in claim 2, wherein said compensation circuit comprises:
   a second sensing circuit to detect the changing magnetic fields;
   said compensation circuit, operatively connected to said second sensing circuit and responsive thereto, to synchronize application of said compensation voltage with the sensed changing magnetic fields.

4. The medical apparatus as claimed in claim 1, wherein said compensation circuit comprises:
   a sensing circuit to detect the changing magnetic fields;
   said compensation circuit, operatively connected to said sensing circuit and responsive thereto, to synchronize application of said compensation voltage with the sensed changing magnetic fields.

5. The medical apparatus as claimed in claim 1, wherein said compensation circuit is located said proximal end of said first lead.

6. The medical apparatus as claimed in claim 1, wherein said compensation circuit is located within said medical assist device.

7. A medical apparatus, comprising:
   a medical assist device to process signals to relating biological functions;
   a first lead operatively connected to said medical assist device, said first lead having a distal end and a proximal end;
   a second lead operatively connected to said medical assist device, said second lead having a distal end and a proximal end;
   a first electrode operatively connected to said distal end of said first lead;
   a second electrode operatively connected to said distal end of said second lead;
   a filter circuit operatively connected near said distal end of said first lead and said distal end of said second lead; and
   a compensation circuit including a coil that generates a voltage due to a changing MRI electromagnetic field, operatively connected to said first lead, to provide a compensation voltage to enable said filter to effectively block changing magnetic fields induced current in said second lead from passing through said second electrode of said distal end of said second lead.

8. The medical apparatus as claimed in claim 7, wherein said coil is curved in three different spatial directions.

9. The medical apparatus as claimed in claim 7, wherein said compensation circuit further comprises:
   orientation means for changing a spatial orientation of said coil to modify the strength of the voltage induced by the changing MRI electromagnetic field.

10. The medical apparatus as claimed in claim 7 wherein said compensation circuit comprises:
a plurality of coils, each coil generating a voltage due to a changing MRI electromagnetic field such that a combination of voltages due to a changing MRI electromagnetic field are produced.

11. The medical apparatus as claimed in claim 7 wherein said compensation circuit comprises:
three planar coils, each coil generating a voltage due to a changing MRI electromagnetic field such that a combination of voltages due to a changing MRI electromagnetic field are produced.

12. The medical apparatus as claimed in claim 7 wherein said compensation circuit comprises:
a plurality of coils, each coil generating a voltage due to a changing MRI electromagnetic field;
a sensor to measure a strength of voltages induced by the changing MRI electromagnetic field; and
a switching device, operatively connected to said sensor and plurality of coils, to operatively connect a number of said plurality of coils in response to the measured strength of voltages induced by the changing MRI electromagnetic field such that a combination of voltages due to a changing MRI electromagnetic field are produced.

13. The medical apparatus as claimed in claim 7 wherein said compensation circuit comprises:
three planar coils, each coil generating a voltage due to a changing MRI electromagnetic field;
a sensor to measure a strength of voltages induced by the changing MRI electromagnetic field; and
a switching device, operatively connected to said sensor and said coils, to operatively connect a number of said coils in response to the measured strength of voltages induced by the changing MRI electromagnetic field such that a combination of voltages due to a changing MRI electromagnetic field are produced.

14. The medical apparatus as claimed in claim 7 wherein said compensation circuit comprises:
a plurality of coils, each coil generating a voltage due to a changing MRI electromagnetic field;
a transceiver to receive a signal indicating a number of coils to be connected; and
a switching device, operatively connected to said transceiver and plurality of coils, to operatively connect a number of said plurality of coils in response to the received signal indicating the number of coils to be connected such that a combination of voltages due to a changing MRI electromagnetic field.

15. The medical apparatus as claimed in claim 7 wherein said compensation circuit comprises:
three planar coils, each coil generating a voltage due to a changing MRI electromagnetic field;
a transceiver to receive a signal indicating a number of coils to be connected; and
a switching device, operatively connected to said transceiver and said coils, to operatively connect a number of said coils in response to the received signal indicating the number of coils to be connected such that a combination of voltages due to a changing MRI electromagnetic field.

16. A medical apparatus, comprising:
a medical assist device to process signals to relating biological functions;
a first lead operatively connected to said medical assist device, said first lead having a distal end and a proximal end;
a second lead operatively connected to said medical assist device, said second lead having a distal end and a proximal end;
a first electrode operatively connected to said distal end of said first lead;
a second electrode operatively connected to said distal end of said second lead;
a first filter circuit operatively connected near said distal end of said first lead;
a second filter circuit operatively connected near said distal end of said second lead; and
a compensation circuit, operatively connected to said first filter and said second filter, to provide a compensation voltage to enable said first and second filters to effectively block changing magnetic fields induced current in said first and second leads from passing through said first and second electrodes of said distal ends of said first and second leads.

17. The medical apparatus as claimed in claim 16, wherein said first and second filters are capacitors.

18. The medical apparatus as claimed in claim 16, wherein said compensation circuit comprises:
a sensing circuit to detect the changing magnetic fields;
said compensation circuit, operatively connected to said sensing circuit and responsive thereto, to synchronize application of said compensation voltage with the sensed changing magnetic fields.

19. A medical apparatus, comprising:
a medical assist device to process signals to relating biological functions;
a first lead operatively connected to said medical assist device, said first lead having a distal end and a proximal end;
a second lead operatively connected to said medical assist device, said second lead having a distal end and a proximal end;
a first electrode operatively connected to said distal end of said first lead;
a second electrode operatively connected to said distal end of said second lead;
a first filter circuit operatively connected near said distal end of said first lead;
a second filter circuit operatively connected near said distal end of said second lead;
a third filter circuit operatively connected near said proximal end of said first lead;
a fourth filter circuit operatively connected near said proximal end of said second lead; and
a compensation circuit, operatively connected to said first filter and said second filter, to provide a compensation voltage to enable said first and second filters to effectively block changing magnetic fields induced current in said first and second leads from passing through said first and second electrodes of said distal ends of said first and second leads.

20. The medical apparatus as claimed in claim 19, wherein compensation circuit is operatively connected to said third filter and said fourth filter, to provide a compensation voltage to enable said third and fourth filters to effectively block changing magnetic fields induced current in said first and second leads from passing into said medical assist device.

* * * * *